(12) United States Patent
Koehn et al.

(10) Patent No.: US 9,968,090 B2
(45) Date of Patent: May 15, 2018

(54) HERBICIDE-SAFENER COMPOSITIONS CONTAINING N-(1,3,4-OXADIAZOL-2-YL)ARYL CARBOXYLIC ACID AMIDES

(71) Applicant: BAYER CROPSCIENCE AKTIENGESELLSCHAFT, Monheim an Rhein (DE)

(72) Inventors: Arnim Koehn, Klein-Winternheim (DE); Christopher Hugh Rosinger, Hofheim (DE); Elmar Gatzweiler, Bad Nauheim (DE); Hartmut Ahrens, Egelsbach (DE); Simon Doerner-Rieping, Neu-Anspach (DE); Christian Waldraff, Bad Vilbel (DE); Ralf Braun, Ramberg (DE); Ines Heinemann, Hofheim (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days. days.

(21) Appl. No.: 15/025,514

(22) PCT Filed: Sep. 30, 2014

(86) PCT No.: PCT/EP2014/070907
§ 371 (c)(1),
(2) Date: Mar. 28, 2016

(87) PCT Pub. No.: WO2015/049225
PCT Pub. Date: Apr. 9, 2015

(65) Prior Publication Data
US 2016/0235067 A1    Aug. 18, 2016

(30) Foreign Application Priority Data
Oct. 4, 2013 (EP) .................................. 13187355

(51) Int. Cl.
| | | |
|---|---|---|
| A01N 47/32 | (2006.01) |
| A01N 43/82 | (2006.01) |
| A01N 43/72 | (2006.01) |
| A01N 43/34 | (2006.01) |
| A01N 43/40 | (2006.01) |
| A01N 43/42 | (2006.01) |
| A01N 43/56 | (2006.01) |
| A01N 43/653 | (2006.01) |
| A01N 43/76 | (2006.01) |
| A01N 43/80 | (2006.01) |
| A01N 43/84 | (2006.01) |

(52) U.S. Cl.
CPC ............. *A01N 47/32* (2013.01); *A01N 43/42* (2013.01); *A01N 43/56* (2013.01); *A01N 43/653* (2013.01); *A01N 43/76* (2013.01); *A01N 43/80* (2013.01); *A01N 43/82* (2013.01); *A01N 43/84* (2013.01)

(58) Field of Classification Search
None
See application file for complete search history.

(56) References Cited

U.S. PATENT DOCUMENTS

2006/0030485 A1* 2/2006 Ziemer .................. A01N 25/32
504/103
2014/0080705 A1    3/2014 Koehn et al.
2014/0124158 A1    5/2014 Yamashita et al.
2014/0309112 A1   10/2014 Van Almsick et al.

FOREIGN PATENT DOCUMENTS

| WO | 2012/126932 A1 | 9/2012 | |
|---|---|---|---|
| WO | WO 2012126932 A1 * | 9/2012 | ............. A01N 43/82 |
| WO | 2013/064459 A1 | 5/2013 | |
| WO | 2013/08755 A1 | 6/2013 | |

OTHER PUBLICATIONS

International Search Report of PCT/EP2014/070907 dated December 15, 2014.
"Plants Antidotes" (http://knowledge.su/a/antidoty-dlya-rasteniy).

* cited by examiner

*Primary Examiner* — Tracy Vivlemore
*Assistant Examiner* — Monica A Shin
(74) *Attorney, Agent, or Firm* — McBee Moore Woodward & Vanik IP, LLC

(57) ABSTRACT

What are described are herbicide-safener compositions comprising active herbicidal ingredients from the group of the N-(1,3,4-oxadiazol-2-yl)arylcarboxamides and safeners. These herbicide-safener compositions are particularly suitable for use against harmful plants in crops of useful plants.

15 Claims, No Drawings

HERBICIDE-SAFENER COMPOSITIONS CONTAINING N-(1,3,4-OXADIAZOL-2-YL)ARYL CARBOXYLIC ACID AMIDES

CROSS REFERENCE TO RELATED APPLICATIONS

This application is a § 371 National Stage Application of PCT/EP2014/070907, filed Sep. 30, 2014, which claims priority to European 13187355.6 filed Oct. 4, 2013.

BACKGROUND

Field of the Invention

The present invention relates to agrochemically active herbicide-safener compositions, to processes for production thereof and to the use thereof for control of harmful plants.

Description of Related Art

WO 2012/126932 A1 discloses that particular N-(1,3,4-oxadiazol-2-yl)arylcarboxamides have herbicidal properties and control a broad spectrum of weeds. However, not all of these active ingredients are fully compatible with important crop plants, such as cereal species, corn or rice. Therefore, they cannot be used in some crops in such a way as to assure the desired broad herbicidal efficacy against harmful plants.

SUMMARY

It is therefore an object of the present invention to provide herbicidal compositions in which the selectivity of the abovementioned herbicides with respect to important crop plants is increased. This object is achieved by the inventive compositions, described hereinafter, comprising herbicides and safeners.

The present invention provides compositions comprising (A) one or more compounds of the formula (I) or salts thereof,

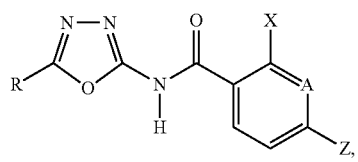

(I)

in which the symbols and indices are defined as follows:
A is N or CY,
R is hydrogen, $(C_1-C_6)$-alkyl, $R^1O-(C_1-C_6)$-alkyl, $CH_2R^6$, $(C_3-C_7)$-cycloalkyl, halo-$(C_1-C_6)$-alkyl, $(C_2-C_6)$-alkenyl, halo-$(C_2-C_6)$-alkenyl, $(C_2-C_6)$-alkynyl, halo-$(C_2-C_6)$-alkynyl, $OR^1$, $NHR^1$, methoxycarbonyl, ethoxycarbonyl, methoxycarbonylmethyl, ethoxycarbonylmethyl, methylcarbonyl, trifluoromethylcarbonyl, dimethylamino, acetylamino, methylsulfenyl, methylsulfinyl, methylsulfonyl, or heteroaryl, heterocyclyl, benzyl or phenyl, each substituted by s radicals from the group consisting of halogen, nitro, cyano, $(C_1-C_6)$-alkyl, halo-$(C_1-C_6)$-alkyl, $(C_3-C_6)$-cycloalkyl, $S(O)_n-(C_1-C_6)$-alkyl, $(C_1-C_6)$-alkoxy, halo-$(C_1-C_6)$-alkoxy and $(C_1-C_6)$-alkoxy-$(C_1-C_4)$-alkyl,
X is nitro, halogen, cyano, formyl, thiocyanato, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_3-C_6)$-alkynyl, $(C_3-C_6)$-cycloalkyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $COR^1$, $COOR^1$, $OCOOR^1$, $NR^1COOR^1$, $C(O)N(R^1)_2$, $NR^1C(O)N(R^1)_2$, $OC(O)N(R^1)_2$, $C(O)NR^1OR^1$, $OR^1$, $OCOR^1$, $OSO_2R^2$, $S(O)_nR^2$, $SO_2OR^1$, $SO_2N(R^1)_2$, $NR^1SO_2R^2$, $NR^1COR^1$, $(C_1-C_6)$-alkyl-$S(O)_nR^2$, $(C_1-C_6)$-alkyl-$OR^1$, $(C_1-C_6)$-alkyl-$OCOR^1$, $(C_1-C_6)$-alkyl-$OSO_2R^2$, $(C_1-C_6)$-alkyl-$CO_2R^1$, $(C_1-C_6)$-alkyl-$SO_2OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $NR_1R_2$, $P(O)(OR^5)_2$, $CH_2P(O)(OR^5)_2$, $(C_1-C_6)$-alkylheteroaryl or $(C_1-C_6)$-alkylheterocyclyl, where the two latter radicals are each substituted by s radicals from the group consisting of halogen, $(C_1-C_6)$-alkyl, halo-$(C_1-C_6)$-alkyl, $S(O)_n-(C_1-C_6)$-alkyl, $(C_1-C_6)$-alkoxy and halo-$(C_1-C_6)$-alkoxy, and where heterocyclyl bears n oxo groups,
Y is hydrogen, nitro, halogen, cyano, thiocyanato, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_2-C_6)$-alkynyl, $(C_3-C_6)$-cycloalkyl, $(C_3-C_6)$-cycloalkenyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $COR^1$, $COOR^1$, $OCOOR^1$, $NR^1COOR^1$, $C(O)N(R^1)_2$, $NR^1C(O)N(R^1)_2$, $OC(O)N(R^1)_2$, $CO(NOR^1)R^1$, $NR^1SO_2R^2$, $NR^1COR^1$, $OR^1$, $OSO_2R^2$, $S(O)_nR^2$, $SO_2OR^1$, $SO_2N(R^1)_2$ $(C_1-C_6)$-alkyl-$S(O)_nR^2$, $(C_1-C_6)$-alkyl-$OR^1$, $(C_1-C_6)$-alkyl-$OCOR^1$, $(C_1-C_6)$-alkyl-$OSO2R^2$, $(C_1-C_6)$-alkyl-$CO_2R^1$, $(C_1-C_6)$-alkyl-CN, $(C_1-C_6)$-alkyl-$SO_2OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $N(R^1)_2$, $P(O)(OR^5)_2$, $CH_2P(O)(OR^5)_2$, $(C_1-C_6)$-alkylphenyl, $(C_1-C_6)$-alkylheteroaryl, $(C_1-C_6)$-alkylheterocyclyl, phenyl, heteroaryl or heterocyclyl, where the six latter radicals are each substituted by s radicals from the group consisting of halogen, nitro, cyano, $(C_1-C_6)$-alkyl, halo-$(C_1-C_6)$-alkyl, $(C_3-C_6)$-cycloalkyl, $S(O)_n-(C_1-C_6)$-alkyl, $(C_1-C_6)$-alkoxy, halo-$(C_1-C_6)$-alkoxy, $(C_1-C_6)$-alkoxy-$(C_1-C_4)$-alkyl and cyanomethyl, and where heterocyclyl bears n oxo groups,
Z halogen, cyano, thiocyanato, $(C_1-C_6)$-alkyl, $(C_1-C_6)$-alkoxy, halo-$(C_1-C_6)$-alkyl, $(C_2-C_6)$-alkenyl, halo-$(C_2-C_6)$-alkenyl, $(C_2-C_6)$-alkynyl, halo-$(C_2-C_6)$-alkynyl, $(C_3-C_6)$-cycloalkyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $COR^1$, $COOR^1$, $OCOOR^1$, $NR^1COOR^1$, $C(O)N(R^1)_2$, $NR^1C(O)N(R^1)_2$, $OC(O)N(R^1)_2$, $C(O)NR^1OR^1$, $OSO_2R^2$, $S(O)_nR^2$, $SO_2OR^1$, $SO_2N(R^1)_2$, $NR^1SO_2R^2$, $NR^1COR^1$, $(C_1-C_6)$-alkyl-$S(O)_nR^2$, $(C_1-C_6)$-alkyl-$OR^1$, $(C_1-C_6)$-alkyl-$OCOR^1$, $(C_1-C_6)$-alkyl-$OSO_2R^2$, $(C_1-C_6)$-alkyl-$CO_2R^1$, $(C_1-C_6)$-alkyl-$SO_2OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $N(R^1)_2$, $P(O)(OR^5)_2$, heteroaryl, heterocyclyl or phenyl, where the three latter radicals are each substituted by s radicals from the group consisting of halogen, nitro, cyano, $(C_1-C_6)$-alkyl, halo-$(C_1-C_6)$-alkyl, $(C_3-C_6)$-cycloalkyl, $S(O)_n-(C_1-C_6)$-alkyl, $(C_1-C_6)$-alkoxy and halo-$(C_1-C_6)$-alkoxy, and where heterocyclyl bears n oxo groups, or
Z may also be hydrogen if Y is the $S(O)_nR^2$ radical,
$R^1$ is hydrogen, $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_2-C_6)$-haloalkynyl, $(C_3-C_6)$-cycloalkyl, $(C_3-C_6)$-cycloalkenyl, $(C_3-C_6)$-halocycloalkyl, $(C_1-C_6)$-alkyl-$O-(C_1-C_6)$-alkyl, $(C_3-C_6)$-cycloalkyl-$(C_1-C_6)$-alkyl, phenyl, phenyl-$(C_1-C_6)$-alkyl, heteroaryl, $(C_1-C_6)$-alkylheteroaryl, heterocyclyl, $(C_1-C_6)$-alkylheterocyclyl, $(C_1-C_6)$-alkyl-O-heteroaryl, $(C_1-C_6)$-alkyl-O-heterocyclyl, $(C_1-C_6)$-alkyl-$NR^3$-heteroaryl, $(C_1-C_6)$-alkyl-$NR^3$-heterocyclyl, where the 21 latter radicals are each substituted by s radicals from the group consisting of cyano, halogen, nitro, thiocyanato, $OR^3$, $S(O)_nR^4$, $N(R^3)_2$, $NR^3OR^3$, $COR^3$, $OCOR^3$, $SCOR^4$, $NR^3COR^3$, $NR^3SO_2R^4$, $CO_2R^3$, $COSR^4$, $CON(R^3)_2$ and $(C_1-C_4)$-alkoxy-$(C_2-C_6)$-alkoxycarbonyl, and where heterocyclyl bears n oxo groups, $R^2$ is $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_2-C_6)$-haloalkynyl, $(C_3-C_6)$-cycloalkyl, $(C_3-C_6)$-cycloalkenyl, $(C_3-C_6)$-halocycloalkyl, $(C_1-C_6)$-alkyl-O—$(C_1-C_6)$-alkyl, $(C_3-C_6)$-cycloalkyl-$(C_1-C_6)$-alkyl, phenyl, phenyl-$(C_1-C_6)$-alkyl, heteroaryl, $(C_1-C_6)$-alkylheteroaryl, heterocyclyl, $(C_1-C_6)$-alkylheterocyclyl, $(C_1-C_6)$-alkyl-O-heteroaryl, $(C_1-C_6)$-alkyl-O-heterocyclyl, $(C_1-C_6)$-alkyl-$NR^3$-heteroaryl, $(C_1-C_6)$-alkyl-$NR^3$-heterocyclyl, where the 21 latter radicals are each substituted by s radicals from the group consisting of cyano, halogen, nitro, thiocyanato, $OR^3$, $S(O)_nR^4$, $N(R^3)_2$, $NR^3OR^3$, $COR^3$, $OCOR^3$, $SCOR^4$, $NR^3COR^3$, $NR^3SO_2R^4$, $CO_2R^3$, $COSR^4$, $CON(R^3)_2$ and $(C_1-C_4)$-alkoxy-$(C_2-C_6)$-alkoxycarbonyl, and where heterocyclyl bears n oxo groups, $R^3$ is hydrogen, $(C_1-C_6)$-alkyl, $(C_2-C_6)$-alkenyl, $(C_2-C_6)$-alkynyl, $(C_3-C_6)$-cycloalkyl or $(C_3-C_6)$-cycloalkyl-$(C_1-C_6)$-alkyl, $R^4$ is $(C_1-C_6)$-alkyl, $(C_2-C_6)$-alkenyl or $(C_2-C_6)$-alkynyl, $R^5$ is methyl or ethyl, $R^6$ is acetoxy, acetamido, N-methylacetamido, benzoyloxy, benzamido, N-methylbenzamido, methoxycarbonyl, ethoxycarbonyl, benzoyl, methylcarbonyl, piperidinylcarbonyl, morpholinylcarbonyl, trifluoromethylcarbonyl, aminocarbonyl, methylaminocarbonyl, dimethylaminocarbonyl, $(C_1-C_6)$-alkoxy, $(C_3-C_6)$-cycloalkyl, or heteroaryl, heterocyclyl or phenyl, each substituted by s radicals from the group consisting of methyl, ethyl, methoxy, trifluoromethyl and halogen, n is 0, 1 or 2, s is 0, 1, 2 or 3, and (B) one or more safeners.

In the formula (I) and all the formulae which follow, alkyl radicals having more than two carbon atoms may be straight-chain or branched. Alkyl radicals are, for example, methyl, ethyl, n- or i-propyl, n-, i-, t- or 2-butyl, pentyls, hexyls such as n-hexyl, i-hexyl and 1,3-dimethylbutyl. Halogen is fluorine, chlorine, bromine or iodine.

Heterocyclyl is a saturated, partly saturated or fully unsaturated cyclic radical which contains 3 to 6 ring atoms, of which 1 to 4 are from the group of oxygen, nitrogen and sulfur, and which may additionally be fused by a benzo ring. For example, heterocyclyl is piperidinyl, pyrrolidinyl, tetrahydrofuranyl, dihydrofuranyl and oxetanyl.

Heteroaryl is an aromatic cyclic radical which contains 3 to 6 ring atoms, of which 1 to 4 are from the group of oxygen, nitrogen and sulfur, and which may additionally be fused by a benzo ring. For example, heteroaryl is benzimidazol-2-yl, furanyl, imidazolyl, isoxazolyl, isothiazolyl, oxazolyl, pyrazinyl, pyrimidinyl, pyridazinyl, pyridinyl, benzisoxazolyl, thiazolyl, pyrrolyl, pyrazolyl, thiophenyl, 1,2,3-oxadiazolyl, 1,2,4-oxadiazolyl, 1,2,5-oxadiazolyl, 1,3,4-oxadiazolyl, 1,2,4-triazolyl, 1,2,3-triazolyl, 1,2,5-triazolyl, 1,3,4-triazolyl, 1,2,4-triazolyl, 1,2,4-thiadiazolyl, 1,3,4-thiadiazolyl, 1,2,3-thiadiazolyl, 1,2,5-thiadiazolyl, 2H-1,2,3,4-tetrazolyl, 1H-1,2,3,4-tetrazolyl, 1,2,3,4-oxatriazolyl, 1,2,3,5-oxatriazolyl, 1,2,3,4-thiatriazolyl and 1,2,3,5-thiatriazolyl.

If a group is polysubstituted by radicals, this is understood to mean that this group is substituted by one or more identical or different radicals from those mentioned.

Depending on the nature of the substituents and the manner in which they are attached, the compounds of the general formula (I) may be present as stereoisomers. If, for example, one or more asymmetric carbon atoms are present, enantiomers and diastereomers may occur. Stereoisomers likewise occur when n is 1 (sulfoxides). Stereoisomers can be obtained from the mixtures obtained in the preparation by customary separation methods, for example by chromatographic separation processes. It is likewise possible to selectively prepare stereoisomers by using stereoselective reactions with use of optically active starting materials and/or auxiliaries. The invention also relates to all the stereoisomers and mixtures thereof that are encompassed by the general formula (I) but are not defined specifically.

Preference is given to inventive compositions which comprise, as herbicide (A), those compounds of the general formula (I) and salts thereof in which A is N or CY, R is hydrogen, $(C_1-C_6)$-alkyl, $(C_3-C_7)$-cycloalkyl, halo-$(C_1-C_6)$-alkyl, $(C_3-C_7)$-cycloalkylmethyl, methoxycarbonylmethyl, ethoxycarbonylmethyl, acetylmethyl, methoxymethyl, methoxyethyl, benzyl, pyrazin-2-yl, furan-2-yl, tetrahydrofuran-2-yl, morpholine, dimethylamino, or phenyl substituted by s radicals from the group of methyl, methoxy, trifluoromethyl and halogen;

X is nitro, halogen, cyano, $(C_1-C_6)$-alkyl, halo-$(C_1-C_6)$-alkyl, $(C_3-C_6)$-cycloalkyl, $OR^1$, $S(O)_nR^2$, $(C_1-C_6)$-alkyl-S$(O)_nR^2$, $(C_1-C_6)$-alkyl-$OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $(C_1-C_6)$-alkylheteroaryl, $(C_1-C_6)$-alkylheterocyclyl, where the two latter radicals are each substituted by s halogen, $(C_1-C_6)$-alkyl, halo-$(C_1-C_6)$-alkyl, $S(O)_n$—$(C_1-C_6)$-alkyl, $(C_1-C_6)$-alkoxy, halo-$(C_1-C_6)$-alkoxy radicals, and where heterocyclyl bears n oxo groups, Y hydrogen, nitro, halogen, cyano, $(C_1-C_6)$-alkyl, $(C_1-C_6)$-haloalkyl, $OR^1$, $S(O)_nR^2$, $SO_2N(R^1)_2$, $N(R^1)_2$, $NR^1SO_2R^2$, $NR^1COR^1$, $(C_1-C_6)$-alkyl-$S(O)_nR^2$, $(C_1-C_6)$-alkyl-$OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $(C_1-C_6)$-alkylphenyl, $(C_1-C_6)$-alkylheteroaryl, $(C_1-C_6)$-alkylheterocyclyl, phenyl, heteroaryl or heterocyclyl, where the 6 latter radicals are each substituted by s radicals from the group of halogen, nitro, cyano, $(C_1-C_6)$-alkyl, halo-$(C_1-C_6)$-alkyl, $(C_3-C_6)$-cycloalkyl, $S(O)_n$—$(C_1-C_6)$-alkyl, $(C_1-C_6)$-alkoxy, halo-$(C_1-C_6)$-alkoxy, $(C_1-C_6)$-alkoxy-$(C_1-C_4)$-alkyl and cyanomethyl, and where heterocyclyl bears n oxo groups, Z is halogen, cyano, nitro, methyl, halo-$(C_1-C_6)$-alkyl, $(C_3-C_6)$-cycloalkyl, $S(O)_nR^2$, 1,2,4-triazol-1-yl, pyrazol-1-yl, or Z may also be hydrogen if Y is the $S(O)_nR^2$ radical, $R^1$ is hydrogen, $(C_1-C_6)$-alkyl, $(C_2-C_6)$-alkenyl, $(C_2-C_6)$-alkynyl, $(C_3-C_6)$-cycloalkyl, $(C_3-C_6)$-cycloalkyl-$(C_1-C_6)$-alkyl, $(C_1-C_6)$-alkyl-O—$(C_1-C_6)$-alkyl, phenyl, phenyl-$(C_1-C_6)$-alkyl, heteroaryl, $(C_1-C_6)$-alkylheteroaryl, heterocyclyl, $(C_1-C_6)$-alkylheterocyclyl, $(C_1-C_6)$-alkyl-O-heteroaryl, $(C_1-C_6)$-alkyl-O-heterocyclyl, $(C_1-C_6)$-alkyl-$NR^3$-heteroaryl or $(C_1-C_6)$-alkyl-$NR^3$-heterocyclyl, where the 16 latter radicals are substituted by s radicals from the group consisting of cyano, halogen, nitro, $OR^3$, $S(O)_nR^4$, $N(R^3)_2$, $NR^3OR^3$, $COR^3$, $OCOR^3$, $NR^3COR^3$, $NR^3SO_2R^4$, $CO_2R^3$, $CON(R^3)_2$ and $(C_1-C_4)$-alkoxy-$(C_2-C_6)$-alkoxycarbonyl, and where heterocyclyl bears n oxo groups, $R^2$ is $(C_1-C_6)$-alkyl, $(C_3-C_6)$-cycloalkyl or $(C_3-C_6)$-cycloalkyl-$(C_1-C_6)$-alkyl, where these three aforementioned radicals are each substituted by s radicals from the group consisting of halogen and $OR^3$, $R^3$ is hydrogen or $(C_1-C_6)$-alkyl, $R^4$ is $(C_1-C_6)$-alkyl, n is 0, 1 or 2,
s is 0, 1, 2 or 3.

DETAILED DESCRIPTION OF A PREFERRED EMBODIMENT

Particular preference is given to inventive compositions which comprise, as herbicide (A), those compounds of the general formula (I) and salts thereof in which
A is N or CY,
R is Me, Et, c-Pr, $CH_2OMe$, $CH_2OEtCH_2F$, $CHF_2$ or pyrazin-2-yl,
X is H, Cl, Br, Me or $CH_2OMe$,
Y is $OCHF_2$, $OCH_2CF_3$, $OCH_2CH_2F$ $CH_2OCH_2CF_3$, $OCH_2CH_2SCF_3$, $OCH_2CH_2CH_2OMe$, $OCH_2$-cPr, $OCH_2CH_2OEt$, $OCH_2CH_2Cl$, $OCH_2CH_2CH_2SMe$, $SO_2Me$, $SO_2Et$, SOMe, SMe, OMe, OEt, O-nPr, O-propargyl, 4-OMe-1H-pyrazol-1-yl, $SCH_2$-c-Pr, SEt, 5-cyano-4,5-dihydro-1,2-oxazol-3-yl, 2H-1,2,3-triazol-2-yl, 1H-1,2,3-triazol-1-yl, 1H-pyrazol-1-yl, 5-ethyl-4,5-dihydro-1,2-oxazol-3-yl, N(Me)CHO or N(CO)-pyrrolidine,
Z is Cl, Me, $SO_2Me$, $SO_2Et$, $CF_3$ or $C_2F_5$.

Examples of compounds particularly preferred as herbicide (A) are listed in the tables which follow.

The abbreviations used here are:
Et=ethyl  Me=methyl  nPr=n-propyl  i-Pr=isopropyl  c-Pr=cyclopropyl  Ph=phenyl  Ac=acetyl

TABLE 1

Compounds of the general formula (I) in which A is CY

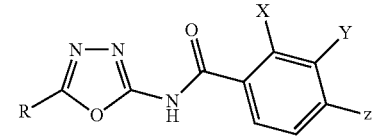

| Ex. no. | R | X | Y | Z |
|---|---|---|---|---|
| A1-1 | Me | Cl | $CH_2OCH_2CF_3$ | $SO_2Me$ |
| A1-2 | c-Pr | Cl | $SO_2Me$ | $CF_3$ |
| A1-3 | $CH_2OMe$ | Me | $SO_2Me$ | $CF_3$ |
| A1-4 | Me | Me | OEt | $SO_2Me$ |
| A1-5 | Me | Cl | OEt | $SO_2Me$ |
| A1-6 | Me | Cl | SEt | $CF_3$ |
| A1-7 | Me | Cl | $SO_2Et$ | $CF_3$ |
| A1-8 | Et | Me | $SO_2Me$ | $CF_3$ |
| A1-9 | $CH_2OMe$ | Br | $SO_2Me$ | $CF_3$ |
| A1-10 | Me | Cl | 5-cyano-4,5-dihydro-1,2-oxazol-3-yl | $SO_2Et$ |
| A1-11 | $CH_2OMe$ | Me | SMe | $CF_3$ |
| A1-12 | Et | Cl | $SO_2Me$ | $CF_3$ |
| A1-13 | Me | Me | $SO_2Me$ | $CF_3$ |
| A1-14 | Me | Cl | SOMe | $CF_3$ |
| A1-15 | $CH_2OEt$ | Cl | $SO_2Me$ | $CF_3$ |
| A1-16 | Me | Cl | 2H-1,2,3-triazol-2-yl | $SO_2Me$ |
| A1-17 | Me | Cl | O—$CH_2CH_2SMe$ | Cl |
| A1-18 | Me | Cl | $OCH_2CH_2OCF_3$ | $SO_2Et$ |
| A1-19 | Me | Cl | $OCH_2CF_3$ | $SO_2Me$ |
| A1-20 | Me | Cl | $SO_2Me$ | Me |
| A1-21 | Me | $CH_2OMe$ | $SO_2Me$ | $CF_3$ |
| A1-22 | Me | Cl | $OCH_2CH_2OEt$ | $SO_2Et$ |
| A1-23 | Me | Cl | $OCH_2CH_2Cl$ | $SO_2Et$ |
| A1-24 | Et | Cl | 5-cyano-4,5-dihydro-1,2-oxazol-3-yl | $SO_2Et$ |
| A1-25 | Me | Me | SMe | $CF_3$ |
| A1-26 | Me | Cl | $OCH_2CH_2Cl$ | $SO_2Me$ |
| A1-27 | Me | Cl | $OCH_2CH_2CH_2SMe$ | Cl |
| A1-28 | Me | Cl | $SCH_2$-c-Pr | $CF_3$ |
| A1-29 | $CH_2F$ | Me | $SO_2Me$ | $CF_3$ |
| A1-30 | Me | Cl | O-propargyl | $SO_2Me$ |
| A1-31 | Me | Cl | 1H-1,2,3-triazol-1-yl | $CF_3$ |

TABLE 1-continued

Compounds of the general formula (I) in which A is CY

| Ex. no. | R | X | Y | Z |
|---|---|---|---|---|
| A1-32 | H | Cl | $CH_2OCH_2CF_3$ | $SO_2Me$ |
| A1-33 | Me | Cl | 5-cyano-4,5-dihydro-1,2-oxazol-3-yl | $SO_2Me$ |
| A1-34 | c-Pr | Me | SOMe | $CF_3$ |
| A1-35 | Et | Cl | $SO_2Me$ | $SO_2Me$ |
| A1-36 | Me | Cl | $SO_2Me$ | $CF_3$ |
| A1-37 | Me | Me | 4,5-dihydro-1,2-oxazol-3-yl | $SO_2Me$ |
| A1-38 | Me | Me | 1H-pyrazol-1-yl | $SO_2Me$ |
| A1-39 | Me | Cl | O—nPr | $SO_2Me$ |
| A1-40 | Me | Cl | $OCH_2CH_2CH_2OMe$ | $SO_2Et$ |
| A1-41 | Me | Cl | O—nPr | $SO_2Et$ |
| A1-42 | $CH_2OMe$ | Cl | SOMe | $CF_3$ |
| A1-43 | $CH_2OMe$ | Cl | $SO_2Me$ | $CF_3$ |
| A1-44 | Me | Cl | 5-ethyl-4,5-dihydro-1,2-oxazol-3-yl | Cl |
| A1-45 | Me | Me | N(Me)CHO | $CF_3$ |
| A1-46 | Me | Cl | N(CO)-pyrrolidine | Cl |
| A1-47 | $CF_3$ | Me | $SO_2Me$ | $SO_2Me$ |
| A1-48 | Me | Me | 4-OMe-1H-pyrazol-1-yl | $SO_2Me$ |
| A1-49 | Me | Me | 1H-1,2,3-triazol-1-yl | $SO_2Me$ |
| A1-50 | Me | Cl | $OCH_2CH_2CH_2OMe$ | $SO_2Me$ |
| A1-51 | Me | Cl | $OCHF_2$ | $SO_2Me$ |
| A1-52 | Me | Me | 1H-pyrazol-1-yl | $CF_3$ |
| A1-53 | Me | Cl | $OCH_2CH_2CH_2SCF_3$ | $SO_2Me$ |
| A1-54 | $CHF_2$ | Me | $SO_2Me$ | $CF_3$ |
| A1-55 | Me | Cl | 1H-pyrazol-1-yl | $CF_3$ |
| A1-56 | Me | Cl | $OCH_2$—cPr | $SO_2Me$ |
| A1-57 | Me | Cl | $OCH_2CH_2F$ | $SO_2Me$ |
| A1-58 | Me | Me | SMe | $C_2F_5$ |
| A1-59 | Me | Cl | OMe | $SO_2Me$ |
| A1-60 | Me | Me | SOMe | $CF_3$ |
| A1-61 | Me | Br | OEt | $SO_2Me$ |
| A1-62 | $(CH_2)_2OMe$ | Me | $SO_2Me$ | $CF_3$ |
| A1-63 | Me | Cl | $SOCH_2$c-Pr | $CF_3$ |
| A1-64 | Me | Cl | SOMe | $C_2F_5$ |
| A1-65 | Me | Me | 1H-pyrazol-1-yl | $CF_3$ |
| A1-66 | Me | Cl | 4-methyl-1H-pyrazol-1-yl | $SO_2Me$ |
| A1-67 | Me | Et | $SO_2Et$ | $CF_3$ |
| A1-68 | Me | Cl | $OCH_2CH_2SEt$ | Cl |
| A1-69 | Me | OMe | SOEt | $CF_3$ |

TABLE 2

Compounds of the general formula (I) in which A is nitrogen

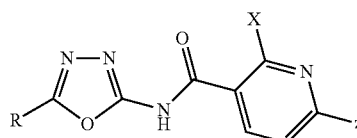

| Ex. no. | R | X | Z |
|---|---|---|---|
| A2-1 | Me | Me | $CF_3$ |
| A2-2 | pyrazin-2-yl | Cl | $CF_3$ |
| A2-3 | Me | Br | $CF_3$ |
| A2-4 | Me | Cl | $CF_3$ |

The application rate of the herbicides (A) can vary within a wide range with the outdoor conditions, such as temperature, humidity and the type of herbicide used, for example between 0.001 g and 2000 g a.i./ha (ai/ha hereinafter means "active substance per hectare"=based on 100% active ingredient).

In the case of pre- and post-emergence applications at application rates of 0.01 g to 1000 g a.i./ha of the herbicides (A), a relatively broad spectrum of harmful plants, for example annual and perennial mono- or dicotyledonous weeds, and of unwanted crop plants is controlled. For the inventive compositions, the application rates are generally relatively low, for example in the range from 0.1 g to 800 g a.i./ha, preferably 1 g to 500 g a.i./ha, more preferably 10 g to 400 g a.i./ha.

The herbicides (A) are suitable for control of harmful plants, for example, in plant crops, for example in economically important farm crops, e.g. monocotyledonous farm crops such as cereals (e.g. wheat, barley, rye, oats), rice, corn, millet/sorghum, or dicotyledonous farm crops such as sugar beet, oilseed rape, cotton, sunflower and legumes, for example of the genera *Glycine* (e.g. *Glycine max.* (soya) such as non-transgenic *Glycine max.* (e.g. conventional varieties such as STS varieties) or transgenic *Glycine max.* (e.g. RR soya or LL soya) and crosses thereof), *Phaseolus, Pisum, Vicia* and *Arachis*, or vegetable crops from various botanic groups, such as potato, leek, cabbage, carrot, tomato, onion, and permanent crops and plantation crops such as pome fruit and stone fruit, berries, grapes, hevea, bananas, sugar cane, coffee, tea, citrus, nut plantations, lawns, palm crops and forestry crops. For the use of the inventive herbicide-safener compositions (A)+(B), these crops are likewise preferred, particular preference being given to use in cereals (e.g. wheat, barley, rye, oats), rice, corn, millet/sorghum, sugar beet, sugar cane, sunflower, oilseed rape and cotton. The herbicide-safener compositions (A)+(B) are also usable in tolerant and nontolerant mutant crops and tolerant and nontolerant transgenic crops, preferably of corn, rice, cereals, oilseed rape and soya, for example those which are resistant to imidazolinone herbicides, atrazine, glufosinate or glyphosate.

The herbicides (A) are known from WO 2012/126932 A1 and can be obtained by the processes described therein.

The safeners present as component (B) are understood to mean compounds suitable for reducing phytotoxic effects of active ingredients in crop protection compositions, such as herbicides, on crop plants.

In the context of the present invention, the herbicides (A) are combined with the following safener compounds:

S1) Compounds from the group of heterocyclic carboxylic acid derivatives:

S1$^a$) Compounds of the dichlorophenylpyrazoline-3-carboxylic acid type (S1$^a$), preferably compounds such as 1-(2,4-dichlorophenyl)-5-(ethoxycarbonyl)-5-methyl-2-pyrazoline-3-carboxylic acid, ethyl 1-(2,4-dichlorophenyl)-5-(ethoxycarbonyl)-5-methyl-2-pyrazoline-3-carboxylate (S1-1) ("mefenpyr-diethyl"), and related compounds as described in WO-A-91/07874;

S1$^b$) Derivatives of dichlorophenylpyrazolecarboxylic acid (S1$^b$), preferably compounds such as ethyl 1-(2,4-dichlorophenyl)-5-methylpyrazole-3-carboxylate (S1-2), ethyl 1-(2,4-dichlorophenyl)-5-isopropylpyrazole-3-carboxylate (S1-3), ethyl 1-(2,4-dichlorophenyl)-5-(1,1-dimethylethyl)pyrazole-3-carboxylate (S1-4) and related compounds as described in EP-A-333 131 and EP-A-269 806;

S1$^c$) Derivatives of 1,5-diphenylpyrazole-3-carboxylic acid (SiC), preferably compounds such as ethyl 1-(2,4-dichlorophenyl)-5-phenylpyrazole-3-carboxylate (S1-5), methyl 1-(2-chlorophenyl)-5-phenylpyrazole-3-carboxylate (S1-6) and related compounds as described, for example, in EP-A-268554;

S1$^d$) Compounds of the triazolecarboxylic acid type (S1$^d$), preferably compounds such as fenchlorazole (ethyl ester), i.e. ethyl 1-(2,4-dichlorophenyl)-5-trichloromethyl-1H-1,2,4-triazole-3-carboxylate (S1-7), and related compounds, as described in EP-A-174 562 and EP-A-346 620;

S1$^e$) Compounds of the 5-benzyl- or 5-phenyl-2-isoxazoline-3-carboxylic acid type or of the 5,5-diphenyl-2-isoxazoline-3-carboxylic acid type (S1$^e$), preferably compounds such as ethyl 5-(2,4-dichlorobenzyl)-2-isoxazoline-3-carboxylate (S1-8) or ethyl 5-phenyl-2-isoxazoline-3-carboxylate (S1-9) and related compounds as described in WO-A-91/08202, or 5,5-diphenyl-2-isoxazolinecarboxylic acid (S1-10) or ethyl 5,5-diphenyl-2-isoxazolinecarboxylate (S1-11) ("isoxadifen-ethyl") or n-propyl 5,5-diphenyl-2-isoxazolinecarboxylate (S1-12) or ethyl 5-(4-fluorophenyl)-5-phenyl-2-isoxazoline-3-carboxylate (S1-13), as described in patent application WO-A-95/07897.

S2) Compounds from the group of the 8-quinolinyloxy derivatives (S2):

S2$^a$) Compounds of the 8-quinolinoxyacetic acid type (S2$^a$), preferably 1-methylhexyl (5-chloro-8-quinolinoxy)acetate ("cloquintocet-mexyl") (S2-1), 1,3-dimethylbut-1-yl (5-chloro-8-quinolinoxy)acetate (S2-2),
4-allyloxybutyl (5-chloro-8-quinolinoxy)acetate (S2-3), 1-allyloxyprop-2-yl (5-chloro-8-quinolinoxy)acetate (S2-4), ethyl (5-chloro-8-quinolinoxy)acetate (S2-5), methyl (5-chloro-8-quinolinoxy)acetate (S2-6), allyl (5-chloro-8-quinolinoxy)acetate (S2-7), 2-(2-propylideneiminoxy)-1-ethyl (5-chloro-8-quinolinoxy)acetate (S2-8), 2-oxoprop-1-yl (5-chloro-8-quinolinoxy) acetate (S2-9) and related compounds, as described in EP-A-86 750, EP-A-94 349 and EP-A-191 736 or EP-A-0 492 366, and also (5-chloro-8-quinolinoxy) acetic acid (S2-10), hydrates and salts thereof, for example the lithium, sodium, potassium, calcium, magnesium, aluminum, iron, ammonium, quaternary ammonium, sulfonium or phosphonium salts thereof, as described in WO-A-2002/34048;

S2$^b$) Compounds of the (5-chloro-8-quinolinoxy)malonic acid type (S2$^b$), preferably compounds such as diethyl (5-chloro-8-quinolinoxy)malonate, diallyl (5-chloro-8-quinolinoxy)malonate, methyl ethyl (5-chloro-8-quinolinoxy)malonate and related compounds, as described in EP-A-0 582 198.

S3) Active ingredients of the dichloroacetamide type (S3), which are frequently used as pre-emergence safeners (soil-acting safeners), for example
"dichlormid" (N,N-diallyl-2,2-dichloroacetamide) (S3-1),
"R-29148" (3-dichloroacetyl-2,2,5-trimethyl-1,3-oxazolidine) from Stauffer (S3-2),
"R-28725" (3-dichloroacetyl-2,2-dimethyl-1,3-oxazolidine) from Stauffer (S3-3),
"benoxacor" (4-dichloroacetyl-3,4-dihydro-3-methyl-2H-1,4-benzoxazine) (S3-4),
"PPG-1292" (N-allyl-N-[(1,3-dioxolan-2-yl)methyl]dichloroacetamide) from PPG Industries (S3-5),
"DKA-24" (N-allyl-N-[(allylaminocarbonyl)methyl]dichloroacetamide) from Sagro-Chem (S3-6),
"AD-67" or "MON 4660" (3-dichloroacetyl-1-oxa-3-azaspiro[4.5]decane) from Nitrokemia or Monsanto (S3-7),
"TI-35" (1-dichloroacetylazepane) from TRI-Chemical RT (S3-8),
"diclonon" (dicyclonon) (synonym: "BAS 145138" or "LAB145138") (RS)-1-dichloroacetyl-3,3,8a-trimethylperhydropyrrolo[1,2-a]pyrimidin-6-one from BASF (S3-9), "furilazole" or "MON 13900" ((RS)-3-dichloroacetyl-5-(2-furyl)-2,2-dimethyloxazolidine) (S3-10), and the (R) isomer thereof (S3-11).

S4) Compounds from the class of the acylsulfonamides (S4):

S4$^a$) N-Acylsulfonamides of the formula (S4$^a$) and salts thereof, as described in WO-A-97/45016,

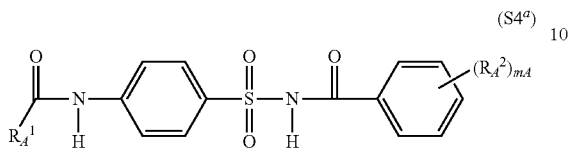

(S4$^a$)

in which $R_A^1$ is ($C_1$-$C_6$)-alkyl or ($C_3$-$C_6$)-cycloalkyl, where these radicals are substituted by $v_A$ substituents from the group of halogen, ($C_1$-$C_4$)-alkoxy, ($C_1$-$C_6$)-haloalkoxy and ($C_1$-$C_4$)-alkylthio and, in the case of cyclic radicals, also by ($C_1$-$C_4$)-alkyl and ($C_1$-$C_4$)-haloalkyl;

$R_A^2$ is halogen, ($C_1$-$C_4$)-alkyl, ($C_1$-$C_4$)-alkoxy, $CF_3$;

$m_A$ is 1 or 2;

$v_A$ is 0, 1, 2 or 3.

S4$^b$) Compounds of the 4-(benzoylsulfamoyl)benzamide type of the formula (S4$^b$) and salts thereof, as described in WO-A-99/16744,

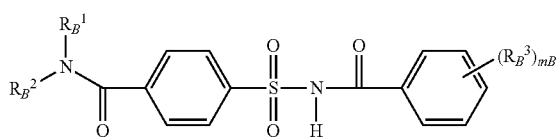

(S4$^b$)

in which $R_B^1$, $R_B^2$ are each independently hydrogen, ($C_1$-$C_6$)-alkyl, ($C_3$-$C_6$)-cycloalkyl, ($C_3$-$C_6$)-alkenyl or ($C_3$-$C_6$)-alkynyl, $R_B^3$ is halogen, ($C_1$-$C_4$)-alkyl, ($C_1$-$C_4$)-haloalkyl or ($C_1$-$C_4$)-alkoxy and $m_B$ is 1 or 2, for example those in which $R_B^1$=cyclopropyl, $R_B^2$=hydrogen and ($R_B^3$)=2-OMe (S4-1, "cyprosulfamide"), $R_B^1$=cyclopropyl, $R_B^2$=hydrogen and ($R_B^3$)=5-Cl-2-OMe (S4-2), $R_B^1$=ethyl, $R_B^2$=hydrogen and ($R_B^3$)=2-OMe (S4-3), $R_B^1$=isopropyl, $R_B^2$=hydrogen and ($R_B^3$)=5-Cl-2-OMe (S4-4) and $R_B^1$=isopropyl, $R_B^2$=hydrogen and ($R_B^3$)=2-OMe (S4-5).

S4$^c$) Compounds from the class of the benzoylsulfamoylphenylureas of the formula (S4c), as described in EP-A-365484,

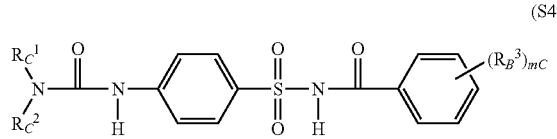

(S4$^c$)

in which $R_C^1$, $R_C^2$ are each independently hydrogen, ($C_1$-$C_8$)-alkyl, ($C_3$-$C_8$)-cycloalkyl, ($C_3$-$C_6$)-alkenyl or ($C_3$-$C_6$)-alkynyl, $R_C^3$ is halogen, ($C_1$-$C_4$)-alkyl, ($C_1$-$C_4$)-alkoxy or $CF_3$;

$m_C$ is 1 or 2;

for example

1-[4-(N-2-methoxybenzoylsulfamoyl)phenyl]-3-methylurea (S4-6),

1-[4-(N-2-methoxybenzoylsulfamoyl)phenyl]-3,3-dimethylurea,

1-[4-(N-4,5-dimethylbenzoylsulfamoyl)phenyl]-3-methylurea.

S4$^d$) Compounds of the N-phenylsulfonylterephthalamide type of the following formula (S4$^d$) and salts thereof, which are known, for example, from CN 101838227,

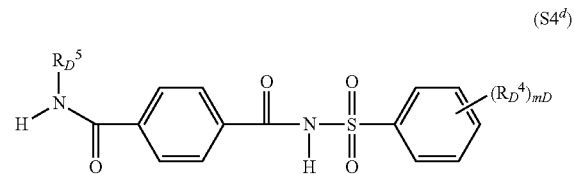

(S4$^d$)

in which $R_D^4$ is halogen, ($C_1$-$C_4$)-alkyl, ($C_1$-$C_4$)-alkoxy or $CF_3$;

$m_D$ is 1 or 2;

$R_D^5$ is hydrogen, ($C_1$-$C_6$)-alkyl, ($C_3$-$C_6$)-cycloalkyl, ($C_2$-$C_6$)-alkenyl, ($C_2$-$C_6$)-alkynyl or ($C_5$-$C_6$)-cycloalkenyl.

S5) Active ingredients from the class of the hydroxyaromatics and the aromatic-aliphatic carboxylic acid derivatives (S5), for example ethyl 3,4,5-triacetoxybenzoate, 3,5-dimethoxy-4-hydroxybenzoic acid, 3,5-dihydroxybenzoic acid, 4-hydroxysalicylic acid, 4-fluorosalicyclic acid, 2-hydroxycinnamic acid, 2,4-dichlorocinnamic acid, as described in WO-A-2004/084631, WO-A-2005/015994, WO-A-2005/016001.

S6) Active ingredients from the class of the 1,2-dihydroquinoxalin-2-ones (S6), for example 1-methyl-3-(2-thienyl)-1,2-dihydroquinoxalin-2-one, 1-methyl-3-(2-thienyl)-1,2-dihydroquinoxaline-2-thione, 1-(2-aminoethyl)-3-(2-thienyl)-1,2-dihydroquinoxalin-2-one hydrochloride, 1-(2-methylsulfonylaminoethyl)-3-(2-thienyl)-1,2-dihydroquinoxalin-2-one, as described in WO-A-2005/112630.

S7) Compounds from the class of the diphenylmethoxyacetic acid derivatives (S7), for example methyl diphenylmethoxyacetate (CAS reg. no. 41858-19-9) (S7-1), ethyl diphenylmethoxyacetate or diphenylmethoxyacetic acid, as described in WO-A-98/38856.

S8) Compounds of the formula (S8), as described in WO-A-98/27049,

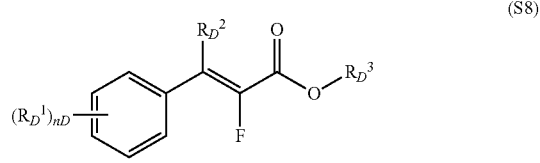

(S8)

in which $R_D^1$ is halogen, ($C_1$-$C_4$)-alkyl, ($C_1$-$C_4$)-haloalkyl, ($C_1$-$C_4$)-alkoxy, ($C_1$-$C_4$)-haloalkoxy, $R_D^2$ is hydrogen or $(C_1$-$C_4)$-alkyl $R_D^3$ is hydrogen, $(C_1$-$C_8)$-alkyl, $(C_2$-$C_4)$-alkenyl, $(C_2$-$C_4)$-alkynyl or aryl, where each of the aforementioned carbon-containing radicals is unsubstituted or substituted by one or more, preferably up to three identical or different radicals from the group consisting of halogen and alkoxy; or salts thereof, $n_D$ is 0, 1 or 2.

S9) Active ingredients from the class of the 3-(5-tetrazolylcarbonyl)-2-quinolones (S9), for example 1,2-dihydro-4-hydroxy-1-ethyl-3-(5-tetrazolylcarbonyl)-2-quinolone (CAS reg. no.: 219479-18-2), 1,2-dihydro-4-hydroxy-1-methyl-3-(5-tetrazolylcarbonyl)-2-quinolone (CAS reg. no. 95855-00-8), as described in WO-A-1999/000020.

S10) Compounds of the formula (S10$^a$) or (S10$^b$) as described in WO-A-2007/023719 and WO-A-2007/023764

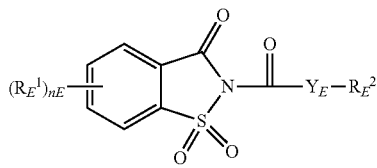

(S10$^a$)

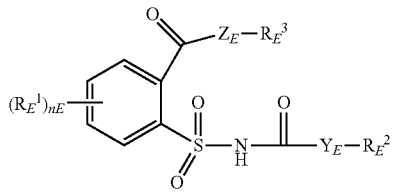

(S10$^b$)

in which $R_E^1$ is halogen, $(C_1$-$C_4)$-alkyl, methoxy, nitro, cyano, $CF_3$, $OCF_3$ $Y_E$, $Z_E$ are each independently O or S, $n_E$ is 0, 1, 2, 3 or 4, $R_E^2$ is $(C_1$-$C_{16})$-alkyl, $(C_2$-$C_6)$-alkenyl, $(C_3$-$C_6)$-cycloalkyl, aryl, benzyl or halobenzyl, $R_E^3$ is hydrogen or $(C_1$-$C_6)$-alkyl.

S11) Active ingredients of the oxyimino compound type (S11), which are known as seed-dressing agents, for example "oxabetrinil" ((Z)-1,3-dioxolan-2-ylmethoxyimino(phenyl)acetonitrile) (S11-1), which is known as a seed-dressing safener for millet/sorghum against metolachlor damage, "fluxofenim" (1-(4-chlorophenyl)-2,2,2-trifluoro-1-ethanone O-(1,3-dioxolan-2-ylmethyl)oxime) (S11-2), which is known as a seed-dressing safener for millet/sorghum against metolachlor damage, and "cyometrinil" or "CGA-43089" ((Z)-cyanomethoxyimino(phenyl)acetonitrile) (S11-3), which is known as a seed-dressing safener for millet/sorghum against metolachlor damage.

S12) Active ingredients from the class of the isothiochromanones (S12), for example methyl [(3-oxo-1H-2-benzothiopyran-4(3H)-ylidene)methoxy]acetate (CAS reg. no. 205121-04-6) (S12-1) and related compounds from WO-A-1998/13361.

S13) One or more compounds from group (S13):

"naphthalic anhydride" (1,8-naphthalenedicarboxylic anhydride) (S13-1), which is known as a seed-dressing safener for corn against thiocarbamate herbicide damage, "fenclorim" (4,6-dichloro-2-phenylpyrimidine) (S13-2), which is known as a safener for pretilachlor in sown rice, "flurazole" (benzyl 2-chloro-4-trifluoromethyl-1,3-thiazole-5-carboxylate) (S13-3), which is known as a seed-dressing safener for millet/sorghum against alachlor and metolachlor damage, "CL 304415" (CAS reg. no. 31541-57-8) (4-carboxy-3,4-dihydro-2H-1-benzopyran-4-acetic acid) (S13-4) from American Cyanamid, which is known as a safener for corn against damage by imidazolinones, "MG 191" (CAS reg. no. 96420-72-3) (2-dichloromethyl-2-methyl-1,3-dioxolane) (S13-5) from Nitrokemia, which is known as a safener for corn, "MG-838" (CAS reg. no. 133993-74-5) (2-propenyl 1-oxa-4-azaspiro[4.5]decane-4-carbodithioate) (S13-6) from Nitrokemia, "disulfoton" (O,O-diethyl S-2-ethylthioethyl phosphorodithioate) (S13-7), "dietholate" (O,O-diethyl O-phenyl phosphorothioate) (S13-8), "mephenate" (4-chlorophenyl methylcarbamate) (S13-9).

S14) Active ingredients which, in addition to herbicidal action against harmful plants, also have safener action on crop plants such as rice, for example "dimepiperate" or "MY-93" (S-1-methyl 1-phenylethylpiperidine-1-carbothioate), which is known as a safener for rice against damage by the herbicide molinate (S14-1), "daimuron" or "SK 23" (1-(1-methyl-1-phenylethyl)-3-p-tolylurea), which is known as a safener for rice against damage by the herbicide imazosulfuron (S14-2), "cumyluron"="JC-940" (3-(2-chlorophenylmethyl)-1-(1-methyl-1-phenylethyl)urea, see JP-A-60087254), which is known as a safener for rice against damage by some herbicides (S14-3), "methoxyphenone" or "NK 049" (3,3'-dimethyl-4-methoxybenzophenone), which is known as a safener for rice against damage by some herbicides, "CSB" (1-bromo-4-(chloromethylsulfonyl)benzene) from Kumiai, (CAS reg. no. 54091-06-4), which is known as a safener against damage by some herbicides in rice.

S15) Compounds of the formula (S15) or tautomers thereof as described in WO-A-2007/131861 and WO-A-2008/131860

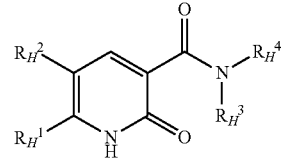

(S15)

in which $R_H^1$ is a $(C_1$-$C_6)$-haloalkyl radical, $R_H^2$ is hydrogen or halogen, $R_H^3$, $R_H^4$ are each independently hydrogen, $(C_1$-$C_{16})$-alkyl, $(C_2$-$C_{16})$-alkenyl or $(C_2$-$C_{16})$-alkynyl, where each of the 3 latter radicals is unsubstituted or substituted by one or more radicals from the group of halogen, hydroxyl, cyano, $(C_1$-$C_4)$-alkoxy, $(C_1$-$C_4)$-haloalkoxy, $(C_1$-$C_4)$-alkylthio, $(C_1$-$C_4)$-alkylamino, di[$(C_1$-$C_4)$-alkyl]amino, [$(C_1$-$C_4)$-alkoxy]carbonyl, [$(C_1$-$C_4)$-haloalkoxy]carbonyl, $(C_3$-$C_6)$-cycloalkyl which is unsubstituted or substituted, phenyl which is unsubstituted or substituted, and heterocyclyl which is unsubstituted or substituted, or ($C_3$-$C_6$)-cycloalkyl, ($C_4$-$C_6$)-cycloalkenyl, ($C_3$-$C_6$)-cycloalkyl fused on one side of the ring to a 4 to 6-membered saturated or unsaturated carbocyclic ring, or ($C_4$-$C_6$)-cycloalkenyl fused on one side of the ring to a 4 to 6-membered saturated or unsaturated carbocyclic ring, where each of the 4 latter radicals is unsubstituted or substituted by one or more radicals from the group of halogen, hydroxyl, cyano, ($C_1$-$C_4$)-alkyl, ($C_1$-$C_4$)-haloalkyl, ($C_1$-$C_4$)-alkoxy, ($C_1$-$C_4$)-haloalkoxy, ($C_1$-$C_4$)-alkylthio, ($C_1$-$C_4$)-alkylamino, di[($C_1$-$C_4$)-alkyl]amino, [($C_1$-$C_4$)-alkoxy]carbonyl, [($C_1$-$C_4$)-haloalkoxy]carbonyl, ($C_3$-$C_6$)-cycloalkyl which is unsubstituted or substituted, phenyl which is unsubstituted or substituted, and heterocyclyl which is unsubstituted or substituted, or $R_H^3$ and $R_H^4$ together with the directly bonded nitrogen atom a four- to eight-membered heterocyclic ring which, in addition to the nitrogen atom, may also contain further ring heteroatoms, preferably up to two further ring heteroatoms from the group of N, O and S, and which is unsubstituted or substituted by one or more radicals from the group of halogen, cyano, nitro, ($C_1$-$C_4$)-alkyl, ($C_1$-$C_4$)-haloalkyl, ($C_1$-$C_4$)-alkoxy, ($C_1$-$C_4$)-haloalkoxy and ($C_1$-$C_4$)-alkylthio.

The documents cited contain detailed information regarding preparation processes and starting materials, and name preferred compounds. These documents are explicitly incorporated by reference into this description.

Of particular significance and preference are the safeners S1-1, S1-7, S1-11, S2-1, S3-1, S3-2, S3-4, S3-7, S3-8, S3-10, S3-11, S4-1, S4-5, S4-6, S11-1, S11-2, S11-3, S13-1, S13-2, S13-3, S13-8, S14-1, S14-2 and S14-3.

Examples of preferred compositions of herbicides (A) and safeners (B) are given below.

(A-1)+(S1-1), (A1-1)+(S1-7), (A1-1)+(S1-11), (A1-1)+(S2-1), (A1-1)+(S3-1), (A1-1)+(S3-2), (A1-1)+(S3-4), (A1-1)+(S3-7), (A1-1)+(S3-8), (A1-1)+(S3-10), (A1-1)+(S3-11), (A1-1)+(S4-1), (A1-1)+(S4-5), (A1-1)+(S4-6), (A1-1)+(S11-1), (A1-1)+(S11-2), (A1-1)+(S11-3), (A1-1)+(S13-1), (A1-1)+(S13-2), (A1-1)+(S13-3), (A1-1)+(S13-8), (A1-1)+(S14-1), (A1-1)+(S14-2), (A1-1)+(S14-3), (A1-2)+(S1-1), (A1-2)+(S1-7), (A1-2)+(S1-11), (A1-2)+(S2-1), (A1-2)+(S3-1), (A1-2)+(S3-2), (A1-2)+(S3-4), (A1-2)+(S3-7), (A1-2)+(S3-8), (A1-2)+(S3-10), (A1-2)+(S3-11), (A1-2)+(S4-1), (A1-2)+(S4-5), (A1-2)+(S4-6), (A1-2)+(S11-1), (A1-2)+(S11-2), (A1-2)+(S11-3), (A1-2)+(S13-1), (A1-2)+(S13-2), (A1-2)+(S13-3), (A1-2)+(S13-8), (A1-2)+(S14-1), (A1-2)+(S14-2), (A1-2)+(S14-3), (A1-3)+(S1-1), (A1-3)+(S1-7), (A1-3)+(S1-11), (A1-3)+(S2-1), (A1-3)+(S3-1), (A1-3)+(S3-2), (A1-3)+(S3-4), (A1-3)+(S3-7), (A1-3)+(S3-8), (A1-3)+(S3-10), (A1-3)+(S3-11), (A1-3)+(S4-1), (A1-3)+(S4-5), (A1-3)+(S4-6), (A1-3)+(S11-1), (A1-3)+(S11-2), (A1-3)+(S11-3), (A1-3)+(S13-1), (A1-3)+(S13-2), (A1-3)+(S13-3), (A1-3)+(S13-8), (A1-3)+(S14-1), (A1-3)+(S14-2), (A1-3)+(S14-3), (A1-4)+(S1-1), (A1-4)+(S1-7), (A1-4)+(S1-11), (A1-4)+(S2-1), (A1-4)+(S3-1), (A1-4)+(S3-2), (A1-4)+(S3-4), (A1-4)+(S3-7), (A1-4)+(S3-8), (A1-4)+(S3-10), (A1-4)+(S3-11), (A1-4)+(S4-1), (A1-4)+(S4-5), (A1-4)+(S4-6), (A1-4)+(S11-1), (A1-4)+(S11-2), (A1-4)+(S11-3), (A1-4)+(S13-1), (A1-4)+(S13-2), (A1-4)+(S13-3), (A1-4)+(S13-8), (A1-4)+(S14-1), (A1-4)+(S14-2), (A1-4)+(S14-3), (A1-5)+(S1-1), (A1-5)+(S1-7), (A1-5)+(S1-11), (A1-5)+(S2-1), (A1-5)+(S3-1), (A1-5)+(S3-2), (A1-5)+(S3-4), (A1-5)+(S3-7), (A1-5)+(S3-8), (A1-5)+(S3-10), (A1-5)+(S3-11), (A1-5)+(S4-1), (A1-5)+(S4-5), (A1-5)+(S4-6), (A1-5)+(S11-1), (A1-5)+(S11-2), (A1-5)+(S11-3), (A1-5)+(S13-1), (A1-5)+(S13-2), (A1-5)+(S13-3), (A1-5)+(S13-8), (A1-5)+(S14-1), (A1-5)+(S14-2), (A1-5)+(S14-3), (A1-6)+(S1-1), (A1-6)+(S1-7), (A1-6)+(S1-11), (A1-6)+(S2-1), (A1-6)+(S3-1), (A1-6)+(S3-2), (A1-6)+(S3-4), (A1-6)+(S3-7), (A1-6)+(S3-8), (A1-6)+(S3-10), (A1-6)+(S3-11), (A1-6)+(S4-1), (A1-6)+(S4-5), (A1-6)+(S4-6), (A1-6)+(S11-1), (A1-6)+(S11-2), (A1-6)+(S11-3), (A1-6)+(S13-1), (A1-6)+(S13-2), (A1-6)+(S13-3), (A1-6)+(S13-8), (A1-6)+(S14-1), (A1-6)+(S14-2), (A1-6)+(S14-3), (A1-7)+(S1-1), (A1-7)+(S1-7), (A1-7)+(S1-11), (A1-7)+(S2-1), (A1-7)+(S3-1), (A1-7)+(S3-2), (A1-7)+(S3-4), (A1-7)+(S3-7), (A1-7)+(S3-8), (A1-7)+(S3-10), (A1-7)+(S3-11), (A1-7)+(S4-1), (A1-7)+(S4-5), (A1-7)+(S4-6), (A1-7)+(S11-1), (A1-7)+(S11-2), (A1-7)+(S11-3), (A1-7)+(S13-1), (A1-7)+(S13-2), (A1-7)+(S13-3), (A1-7)+(S13-8), (A1-7)+(S14-1), (A1-7)+(S14-2), (A1-7)+(S14-3), (A1-8)+(S1-1), (A1-8)+(S1-7), (A1-8)+(S1-11), (A1-8)+(S2-1), (A1-8)+(S3-1), (A1-8)+(S3-2), (A1-8)+(S3-4), (A1-8)+(S3-7), (A1-8)+(S3-8), (A1-8)+(S3-10), (A1-8)+(S3-11), (A1-8)+(S4-1), (A1-8)+(S4-5), (A1-8)+(S4-6), (A1-8)+(S11-1), (A1-8)+(S11-2), (A1-8)+(S11-3), (A1-8)+(S13-1), (A1-8)+(S13-2), (A1-8)+(S13-3), (A1-8)+(S13-8), (A1-8)+(S14-1), (A1-8)+(S14-2), (A1-8)+(S14-3), (A1-9)+(S1-1), (A1-9)+(S1-7), (A1-9)+(S1-11), (A1-9)+(S2-1), (A1-9)+(S3-1), (A1-9)+(S3-2), (A1-9)+(S3-4), (A1-9)+(S3-7), (A1-9)+(S3-8), (A1-9)+(S3-10), (A1-9)+(S3-11), (A1-9)+(S4-1), (A1-9)+(S4-5), (A1-9)+(S4-6), (A1-9)+(S11-1), (A1-9)+(S11-2), (A1-9)+(S11-3), (A1-9)+(S13-1), (A1-9)+(S13-2), (A1-9)+(S13-3), (A1-9)+(S13-8), (A1-9)+(S14-1), (A1-9)+(S14-2), (A1-9)+(S14-3), (A1-10)+(S1-1), (A1-10)+(S1-7), (A1-10)+(S1-11), (A1-10)+(S2-1), (A1-10)+(S3-1), (A1-10)+(S3-2), (A1-10)+(S3-4), (A1-10)+(S3-7), (A1-10)+(S3-8), (A1-10)+(S3-10), (A1-10)+(S3-11), (A1-10)+(S4-1), (A1-10)+(S4-5), (A1-10)+(S4-6), (A1-10)+(S11-1), (A1-10)+(S11-2), (A1-10)+(S11-3), (A1-10)+(S13-1), (A1-10)+(S13-2), (A1-10)+(S13-3), (A1-10)+(S13-8), (A1-10)+(S14-1), (A1-10)+(S14-2), (A1-10)+(S14-3), (A1-11)+(S3-2), (A1-11)+(S3-4), (A1-11)+(S3-7), (A1-11)+(S3-8), (A1-11)+(S3-1), (A1-11)+(S3-11), (A1-11)+(S4-1), (A1-11)+(S4-5), (A1-11)+(S4-6), (A1-11)+(S11-1), (A1-11)+(S11-2), (A1-11)+(S11-3), (A1-11)+(S13-1), (A1-11)+(S13-2), (A1-11)+(S13-3), (A1-11)+(S13-8), (A1-11)+(S14-1), (A1-11)+(S14-2), (A1-11)+(S14-3), (A1-12)+(S1-1), (A1-12)+(S1-7), (A1-12)+(S1-11), (A1-12)+(S2-1), (A1-12)+(S3-1), (A1-12)+(S3-2), (A1-12)+(S3-4), (A1-12)+(S3-7), (A1-12)+(S3-8), (A1-12)+(S3-10), (A1-12)+(S3-11), (A1-12)+(S4-1), (A1-12)+(S4-5), (A1-12)+(S4-6), (A1-12)+(S11-1), (A1-12)+(S11-2), (A1-12)+(S11-3), (A1-12)+(S13-1), (A1-12)+(S13-2), (A1-12)+(S13-3), (A1-12)+(S13-8), (A1-12)+(S14-1), (A1-12)+(S14-2), (A1-12)+(S14-3), (A1-13)+(S1-1), (A1-13)+(S1-7), (A1-13)+(S1-11), (A1-13)+(S2-1), (A1-13)+(S3-1), (A1-13)+(S3-2), (A1-13)+(S3-4), (A1-13)+(S3-7), (A1-13)+(S3-8), (A1-13)+(S3-10), (A1-13)+(S3-11), (A1-13)+(S4-1), (A1-13)+(S4-5), (A1-13)+(S4-6), (A1-13)+(S11-1), (A1-13)+(S11-2), (A1-13)+(S11-3), (A1-13)+(S13-1), (A1-13)+(S13-2), (A1-13)+(S13-3), (A1-13)+(S13-8), (A1-13)+(S14-1), (A1-13)+(S14-2), (A1-13)+(S14-3), (A1-14)+(S1-1), (A1-14)+(S1-7), (A1-14)+(S1-11), (A1-14)+(S2-1), (A1-14)+(S3-1), (A1-14)+(S3-2), (A1-14)+(S3-4), (A1-14)+(S3-7), (A1-14)+(S3-8), (A1-14)+(S3-10), (A1-14)+(S3-11), (A1-14)+(S4-1), (A1-14)+(S4-5), (A1-14)+

(S4-6), (A1-14)+(S11-1), (A1-14)+(S11-2), (A1-14)+(S11-3), (A1-14)+(S13-1), (A1-14)+(S13-2), (A1-14)+(S13-3), (A1-14)+(S13-8), (A1-14)+(S14-1), (A1-14)+(S14-2), (A1-14)+(S14-3), (A1-15)+(S1-1), (A1-15)+(S1-7), (A1-15)+(S1-11), (A1-15)+(S2-1), (A1-15)+(S3-1), (A1-15)+(S3-2), (A1-15)+(S3-4), (A1-15)+(S3-7), (A1-15)+(S3-8), (A1-15)+(S3-10), (A1-15)+(S3-11), (A1-15)+(S4-1), (A1-15)+(S4-5), (A1-15)+(S4-6), (A1-15)+(S11-1), (A1-15)+(S11-2), (A1-15)+(S11-3), (A1-15)+(S13-1), (A1-15)+(S13-2), (A1-15)+(S13-3), (A1-15)+(S13-8), (A1-15)+(S14-1), (A1-15)+(S14-2), (A1-15)+(S14-3), (A1-16)+(S1-1), (A1-16)+(S1-7), (A1-16)+(S1-11), (A1-16)+(S2-1), (A1-16)+(S3-1), (A1-16)+(S3-2), (A1-16)+(S3-4), (A1-16)+(S3-7), (A1-16)+(S3-8), (A1-16)+(S3-10), (A1-16)+(S3-11), (A1-16)+(S4-1), (A1-16)+(S4-5), (A1-16)+(S4-6), (A1-16)+(S11-1), (A1-16)+(S11-2), (A1-16)+(S11-3), (A1-16)+(S13-1), (A1-16)+(S13-2), (A1-16)+(S13-3), (A1-16)+(S13-8), (A1-16)+(S14-1), (A1-16)+(S14-2), (A1-16)+(S14-3), (A1-17)+(S1-1), (A1-17)+(S1-7), (A1-17)+(S1-11), (A1-17)+(S2-1), (A1-17)+(S3-1), (A1-17)+(S3-2), (A1-17)+(S3-4), (A1-17)+(S3-7), (A1-17)+(S3-8), (A1-17)+(S3-10), (A1-17)+(S3-11), (A1-17)+(S4-1), (A1-17)+(S4-5), (A1-17)+(S4-6), (A1-17)+(S11-1), (A1-17)+(S11-2), (A1-17)+(S11-3), (A1-17)+(S13-1), (A1-17)+(S13-2), (A1-17)+(S13-3), (A1-17)+(S13-8), (A1-17)+(S14-1), (A1-17)+(S14-2), (A1-17)+(S14-3), (A1-18)+(S1-1), (A1-18)+(S1-7), (A1-18)+(S1-11), (A1-18)+(S2-1), (A1-18)+(S3-1), (A1-18)+(S3-2), (A1-18)+(S3-4), (A1-18)+(S3-7), (A1-18)+(S3-8), (A1-18)+(S3-10), (A1-18)+(S3-11), (A1-18)+(S4-1), (A1-18)+(S4-5), (A1-18)+(S4-6), (A1-18)+(S11-1), (A1-18)+(S11-2), (A1-18)+(S11-3), (A1-18)+(S13-1), (A1-18)+(S13-2), (A1-18)+(S13-3), (A1-18)+(S13-8), (A1-18)+(S14-1), (A1-18)+(S14-2), (A1-18)+(S14-3), (A1-19)+(S1-1), (A1-19)+(S1-7), (A1-19)+(S1-11), (A1-19)+(S2-1), (A1-19)+(S3-1), (A1-19)+(S3-2), (A1-19)+(S3-4), (A1-19)+(S3-7), (A1-19)+(S3-8), (A1-19)+(S3-10), (A1-19)+(S3-11), (A1-19)+(S4-1), (A1-19)+(S4-5), (A1-19)+(S4-6), (A1-19)+(S11-1), (A1-19)+(S11-2), (A1-19)+(S11-3), (A1-19)+(S13-1), (A1-19)+(S13-2), (A1-19)+(S13-3), (A1-19)+(S13-8), (A1-19)+(S14-1), (A1-19)+(S14-2), (A1-19)+(S14-3), (A1-20)+(S1-1), (A1-20)+(S1-7), (A1-20)+(S1-11), (A1-20)+(S2-1), (A1-20)+(S3-1), (A1-20)+(S3-2), (A1-20)+(S3-4), (A1-20)+(S3-7), (A1-20)+(S3-8), (A1-20)+(S3-10), (A1-20)+(S3-11), (A1-20)+(S4-1), (A1-20)+(S4-5), (A1-20)+(S4-6), (A1-20)+(S111-1), (A1-20)+(S11-2), (A1-20)+(S11-3), (A1-20)+(S13-1), (A1-20)+(S13-2), (A1-20)+(S13-3), (A1-20)+(S13-8), (A1-20)+(S14-1), (A1-20)+(S14-2), (A1-20)+(S14-3), (A1-21)+(S1-1), (A1-21)+(S1-7), (A1-21)+(S1-11), (A1-21)+(S2-1), (A1-21)+(S3-1), (A1-21)+(S3-2), (A1-21)+(S3-4), (A1-21)+(S3-7), (A1-21)+(S3-8), (A1-21)+(S3-10), (A1-21)+(S3-11), (A1-21)+(S4-1), (A1-21)+(S4-5), (A1-21)+(S4-6), (A1-21)+(S11-1), (A1-21)+(S11-2), (A1-21)+(S11-3), (A1-21)+(S13-1), (A1-21)+(S13-2), (A1-21)+(S13-3), (A1-21)+(S13-8), (A1-21)+(S14-1), (A1-21)+(S14-2), (A1-21)+(S14-3), (A1-22)+(S1-1), (A1-22)+(S1-7), (A1-22)+(S1-11), (A1-22)+(S2-1), (A1-22)+(S3-1), (A1-22)+(S3-2), (A1-22)+(S3-4), (A1-22)+(S3-7), (A1-22)+(S3-8), (A1-22)+(S3-10), (A1-22)+(S3-11), (A1-22)+(S4-1), (A1-22)+(S4-5), (A1-22)+(S4-6), (A1-22)+(S11-1), (A1-22)+(S11-2), (A1-22)+(S11-3), (A1-22)+(S13-1), (A1-22)+(S13-2), (A1-22)+(S13-3), (A1-22)+(S13-8), (A1-22)+(S14-1), (A1-22)+(S14-2), (A1-22)+(S14-3), (A1-23)+(S1-1), (A1-23)+(S1-7), (A1-23)+(S1-11), (A1-23)+(S2-1), (A1-23)+(S3-1), (A1-23)+(S3-2), (A1-23)+(S3-4), (A1-23)+(S3-7), (A1-23)+(S3-8), (A1-23)+(S3-10), (A1-23)+(S3-11), (A1-23)+(S4-1), (A1-23)+(S4-5), (A1-23)+(S4-6), (A1-23)+(S11-1), (A1-23)+(S11-2), (A1-23)+(S11-3), (A1-23)+(S13-1), (A1-23)+(S13-2), (A1-23)+(S13-3), (A1-23)+(S13-8), (A1-23)+(S14-1), (A1-23)+(S14-2), (A1-23)+(S14-3), (A1-24)+(S1-1), (A1-24)+(S1-7), (A1-24)+(S1-11), (A1-24)+(S2-1), (A1-24)+(S3-1), (A1-24)+(S3-2), (A1-24)+(S3-4), (A1-24)+(S3-7), (A1-24)+(S3-8), (A1-24)+(S3-10), (A1-24)+(S3-11), (A1-24)+(S4-1), (A1-24)+(S4-5), (A1-24)+(S4-6), (A1-24)+(S11-1), (A1-24)+(S11-2), (A1-24)+(S11-3), (A1-24)+(S13-1), (A1-24)+(S13-2), (A1-24)+(S13-3), (A1-24)+(S13-8), (A1-24)+(S14-1), (A1-24)+(S14-2), (A1-24)+(S14-3), (A1-25)+(S1-1), (A1-25)+(S1-7), (A1-25)+(S1-11), (A1-25)+(S2-1), (A1-25)+(S3-1), (A1-25)+(S3-2), (A1-25)+(S3-4), (A1-25)+(S3-7), (A1-25)+(S3-8), (A1-25)+(S3-10), (A1-25)+(S3-11), (A1-25)+(S4-1), (A1-25)+(S4-5), (A1-25)+(S4-6), (A1-25)+(S11-1), (A1-25)+(S11-2), (A1-25)+(S11-3), (A1-25)+(S13-1), (A1-25)+(S13-2), (A1-25)+(S13-3), (A1-25)+(S13-8), (A1-25)+(S14-1), (A1-25)+(S14-2), (A1-25)+(S14-3), (A1-26)+(S1-1), (A1-26)+(S1-7), (A1-26)+(S1-11), (A1-26)+(S2-1), (A1-26)+(S3-1), (A1-26)+(S3-2), (A1-26)+(S3-4), (A1-26)+(S3-7), (A1-26)+(S3-8), (A1-26)+(S3-10), (A1-26)+(S3-11), (A1-26)+(S4-1), (A1-26)+(S4-5), (A1-26)+(S4-6), (A1-26)+(S11-1), (A1-26)+(S11-2), (A1-26)+(S11-3), (A1-26)+(S13-1), (A1-26)+(S13-2), (A1-26)+(S13-3), (A1-26)+(S13-8), (A1-26)+(S14-1), (A1-26)+(S14-2), (A1-26)+(S14-3), (A1-27)+(S1-1), (A1-27)+(S1-7), (A1-27)+(S1-11), (A1-27)+(S2-1), (A1-27)+(S3-1), (A1-27)+(S3-2), (A1-27)+(S3-4), (A1-27)+(S3-7), (A1-27)+(S3-8), (A1-27)+(S3-10), (A1-27)+(S3-11), (A1-27)+(S4-1), (A1-27)+(S4-5), (A1-27)+(S4-6), (A1-27)+(S11-1), (A1-27)+(S11-2), (A1-27)+(S11-3), (A1-27)+(S13-1), (A1-27)+(S13-2), (A1-27)+(S13-3), (A1-27)+(S13-8), (A1-27)+(S14-1), (A1-27)+(S14-2), (A1-27)+(S14-3), (A1-28)+(S1-1), (A1-28)+(S1-7), (A1-28)+(S1-11), (A1-28)+(S2-1), (A1-28)+(S3-1), (A1-28)+(S3-2), (A1-28)+(S3-4), (A1-28)+(S3-7), (A1-28)+(S3-8), (A1-28)+(S3-10), (A1-28)+(S3-11), (A1-28)+(S4-1), (A1-28)+(S4-5), (A1-28)+(S4-6), (A1-28)+(S11-1), (A1-28)+(S11-2), (A1-28)+(S11-3), (A1-28)+(S13-1), (A1-28)+(S13-2), (A1-28)+(S13-3), (A1-28)+(S13-8), (A1-28)+(S14-1), (A1-28)+(S14-2), (A1-28)+(S14-3), (A1-29)+(S1-1), (A1-29)+(S1-7), (A1-29)+(S1-11), (A1-29)+(S2-1), (A1-29)+(S3-1), (A1-29)+(S3-2), (A1-29)+(S3-4), (A1-29)+(S3-7), (A1-29)+(S3-8), (A1-29)+(S3-10), (A1-29)+(S3-11), (A1-29)+(S4-1), (A1-29)+(S4-5), (A1-29)+(S4-6), (A1-29)+(S11-1), (A1-29)+(S11-2), (A1-29)+(S11-3), (A1-29)+(S13-1), (A1-29)+(S13-2), (A1-29)+(S13-3), (A1-29)+(S13-8), (A1-29)+(S14-1), (A1-29)+(S14-2), (A1-29)+(S14-3), (A1-30)+(S1-1), (A1-30)+(S1-7), (A1-30)+(S1-11), (A1-30)+(S2-1), (A1-30)+(S3-1), (A1-30)+(S3-2), (A1-30)+(S3-4), (A1-30)+(S3-7), (A1-30)+(S3-8), (A1-30)+(S3-10), (A1-30)+(S3-11), (A1-30)+(S4-1), (A1-30)+(S4-5), (A1-30)+(S4-6), (A1-30)+(S11-1), (A1-30)+(S11-2), (A1-30)+(S11-3), (A1-30)+(S13-1), (A1-30)+(S13-2), (A1-30)+(S13-3), (A1-30)+(S13-8), (A1-30)+(S14-1), (A1-30)+(S14-2), (A1-30)+(S14-3), (A1-31)+(S1-1), (A1-31)+(S1-7), (A1-31)+(S1-11), (A1-31)+(S2-1), (A1-31)+(S3-1), (A1-31)+(S3-2), (A1-31)+(S3-4), (A1-31)+(S3-7), (A1-31)+(S3-8), (A1-31)+(S3-10), (A1-31)+(S3-11), (A1-31)+(S4-1), (A1-31)+(S4-5), (A1-31)+(S4-6), (A1-31)+(S11-1), (A1-31)+(S11-2), (A1-31)+(S11-3), (A1-31)+(S13-1), (A1-31)+(S13-2), (A1-31)+(S13-3), (A1-31)+(S13-8), (A1-31)+(S14-1), (A1-31)+(S14-2), (A1-31)+(S14-3), (A1-32)+(S1-1), (A1-32)+(S1-7), (A1-32)+(S1-11), (A1-32)+(S2-1), (A1-32)+(S3-1), (A1-32)+(S3-2), (A1-32)+(S3-4), (A1-32)+(S3-7), (A1-32)+(S3-8), (A1-32)+(S3-10), (A1-32)+(S3-11), (A1-32)+(S4-1), (A1-32)+(S4-5), (A1-32)+(S4-6), (A1-32)+(S11-1), (A1-32)+(S11-2), (A1-32)+(S11-3), (A1-32)+(S13-1), (A1-32)+(S13-2), (A1-32)+(S13-3), (A1-32)+(S13-8), (A1-32)+(S14-1), (A1-32)+(S14-2), (A1-32)+(S14-3), (A1-33)+(S1-1), (A1-33)+(S1-7), (A1-33)+(S1-11), (A1-33)+(S2-1), (A1-33)+(S3-1), (A1-33)+(S3-2), (A1-33)+(S3-4), (A1-33)+(S3-7), (A1-33)+(S3-8), (A1-33)+(S3-10), (A1-33)+(S3-11), (A1-33)+(S4-1), (A1-33)+(S4-5), (A1-33)+(S4-6), (A1-33)+(S11-1), (A1-33)+(S11-2), (A1-33)+(S11-3), (A1-33)+(S13-1), (A1-33)+(S13-2), (A1-33)+(S13-3), (A1-33)+(S13-8), (A1-33)+(S14-1), (A1-33)+(S14-2), (A1-33)+(S14-3), (A1-34)+(S1-1), (A1-34)+(S1-7), (A1-34)+(S1-11), (A1-34)+(S2-1), (A1-34)+(S3-1), (A1-34)+(S3-2), (A1-34)+(S3-4), (A1-34)+(S3-7), (A1-34)+(S3-8), (A1-34)+(S3-10), (A1-34)+(S3-11), (A1-34)+(S4-1), (A1-34)+(S4-5), (A1-34)+(S4-6), (A1-34)+(S11-1), (A1-34)+(S11-2), (A1-34)+(S11-3), (A1-34)+(S13-1), (A1-34)+(S13-2), (A1-34)+(S13-3), (A1-34)+(S13-8), (A1-34)+(S14-1), (A1-34)+(S14-2), (A1-34)+(S14-3), (A1-35)+(S1-1), (A1-35)+(S1-7), (A1-35)+(S1-11), (A1-35)+(S2-1), (A1-35)+(S3-1), (A1-35)+(S3-2), (A1-35)+(S3-4), (A1-35)+(S3-7), (A1-35)+(S3-8), (A1-35)+(S3-10), (A1-35)+(S3-11), (A1-35)+(S4-1), (A1-35)+(S4-5), (A1-35)+(S4-6), (A1-35)+(S11-1), (A1-35)+(S11-2), (A1-35)+(S11-3), (A1-35)+(S13-1), (A1-35)+(S13-2), (A1-35)+(S13-3), (A1-35)+(S13-8), (A1-35)+(S14-1), (A1-35)+(S14-2), (A1-35)+(S14-3), (A1-36)+(S1-1), (A1-36)+(S1-7), (A1-36)+(S1-11), (A1-36)+(S2-1), (A1-36)+(S3-1), (A1-36)+(S3-2), (A1-36)+(S3-4), (A1-36)+(S3-7), (A1-36)+(S3-8), (A1-36)+(S3-10), (A1-36)+(S3-11), (A1-36)+(S4-1), (A1-36)+(S4-5), (A1-36)+(S4-6), (A1-36)+(S11-1), (A1-36)+(S11-2), (A1-36)+(S11-3), (A1-36)+(S13-1), (A1-36)+(S13-2), (A1-36)+(S13-3), (A1-36)+(S13-8), (A1-36)+(S14-1), (A1-36)+(S14-2), (A1-36)+(S14-3), (A1-37)+(S1-1), (A1-37)+(S1-7), (A1-37)+(S1-11), (A1-37)+(S2-1), (A1-37)+(S3-1), (A1-37)+(S3-2), (A1-37)+(S3-4), (A1-37)+(S3-7), (A1-37)+(S3-8), (A1-37)+(S3-10), (A1-37)+(S3-11), (A1-37)+(S4-1), (A1-37)+(S4-5), (A1-37)+(S4-6), (A1-37)+(S11-1), (A1-37)+(S11-2), (A1-37)+(S11-3), (A1-37)+(S13-1), (A1-37)+(S13-2), (A1-37)+(S13-3), (A1-37)+(S13-8), (A1-37)+(S14-1), (A1-37)+(S14-2), (A1-37)+(S14-3), (A1-38)+(S1-1), (A1-38)+(S1-7), (A1-38)+(S1-11), (A1-38)+(S2-1), (A1-38)+(S3-1), (A1-38)+(S3-2), (A1-38)+(S3-4), (A1-38)+(S3-7), (A1-38)+(S3-8), (A1-38)+(S3-10), (A1-38)+(S3-11), (A1-38)+(S4-1), (A1-38)+(S4-5), (A1-38)+(S4-6), (A1-38)+(S11-1), (A1-38)+(S11-2), (A1-38)+(S11-3), (A1-38)+(S13-1), (A1-38)+(S13-2), (A1-38)+(S13-3), (A1-38)+(S13-8), (A1-38)+(S14-1), (A1-38)+(S14-2), (A1-38)+(S14-3), (A1-39)+(S1-1), (A1-39)+(S1-7), (A1-39)+(S1-11), (A1-39)+(S2-1), (A1-39)+(S3-1), (A1-39)+(S3-2), (A1-39)+(S3-4), (A1-39)+(S3-7), (A1-39)+(S3-8), (A1-39)+(S3-10), (A1-39)+(S3-11), (A1-39)+(S4-1), (A1-39)+(S4-5), (A1-39)+(S4-6), (A1-39)+(S11-1), (A1-39)+(S11-2), (A1-39)+(S11-3), (A1-39)+(S13-1), (A1-39)+(S13-2), (A1-39)+(S13-3), (A1-39)+(S13-8), (A1-39)+(S14-1), (A1-39)+(S14-2), (A1-39)+(S14-3), (A1-40)+(S1-1), (A1-40)+(S1-7), (A1-40)+(S1-11), (A1-40)+(S2-1), (A1-40)+(S3-1), (A1-40)+(S3-2), (A1-40)+(S3-4), (A1-40)+(S3-7), (A1-40)+(S3-8), (A1-40)+(S3-10), (A1-40)+(S3-11), (A1-40)+(S4-1), (A1-40)+(S4-5), (A1-40)+(S4-6), (A1-40)+(S11-1), (A1-40)+(S11-2), (A1-40)+(S11-3), (A1-40)+(S13-1), (A1-40)+(S13-2), (A1-40)+(S13-3), (A1-40)+(S13-8), (A1-40)+(S14-1), (A1-40)+(S14-2), (A1-40)+(S14-3), (A1-41)+(S1-1), (A1-41)+(S1-7), (A1-41)+(S1-11), (A1-41)+(S2-1), (A1-41)+(S3-1), (A1-41)+(S3-2), (A1-41)+(S3-4), (A1-41)+(S3-7), (A1-41)+(S3-8), (A1-41)+(S3-10), (A1-41)+(S3-11), (A1-41)+(S4-1), (A1-41)+(S4-5), (A1-41)+(S4-6), (A1-41)+(S11-1), (A1-41)+(S11-2), (A1-41)+(S11-3), (A1-41)+(S13-1), (A1-41)+(S13-2), (A1-41)+(S13-3), (A1-41)+(S13-8), (A1-41)+(S14-1), (A1-41)+(S14-2), (A1-41)+(S14-3), (A1-42)+(S1-1), (A1-42)+(S1-7), (A1-42)+(S1-11), (A1-42)+(S2-1), (A1-42)+(S3-1), (A1-42)+(S3-2), (A1-42)+(S3-4), (A1-42)+(S3-7), (A1-42)+(S3-8), (A1-42)+(S3-10), (A1-42)+(S3-11), (A1-42)+(S4-1), (A1-42)+(S4-5), (A1-42)+(S4-6), (A1-42)+(S11-1), (A1-42)+(S11-2), (A1-42)+(S11-3), (A1-42)+(S13-1), (A1-42)+(S13-2), (A1-42)+(S13-3), (A1-42)+(S13-8), (A1-42)+(S14-1), (A1-42)+(S14-2), (A1-42)+(S14-3), (A1-43)+(S1-1), (A1-43)+(S1-7), (A1-43)+(S1-11), (A1-43)+(S2-1), (A1-43)+(S3-1), (A1-43)+(S3-2), (A1-43)+(S3-4), (A1-43)+(S3-7), (A1-43)+(S3-8), (A1-43)+(S3-10), (A1-43)+(S3-11), (A1-43)+(S4-1), (A1-43)+(S4-5), (A1-43)+(S4-6), (A1-43)+(S11-1), (A1-43)+(S11-2), (A1-43)+(S11-3), (A1-43)+(S13-1), (A1-43)+(S13-2), (A1-43)+(S13-3), (A1-43)+(S13-8), (A1-43)+(S14-1), (A1-43)+(S14-2), (A1-43)+(S14-3), (A1-44)+(S1-1), (A1-44)+(S1-7), (A1-44)+(S1-11), (A1-44)+(S2-1), (A1-44)+(S3-1), (A1-44)+(S3-2), (A1-44)+(S3-4), (A1-44)+(S3-7), (A1-44)+(S3-8), (A1-44)+(S3-10), (A1-44)+(S3-11), (A1-44)+(S4-1), (A1-44)+(S4-5), (A1-44)+(S4-6), (A1-44)+(S11-1), (A1-44)+(S11-2), (A1-44)+(S11-3), (A1-44)+(S13-1), (A1-44)+(S13-2), (A1-44)+(S13-3), (A1-44)+(S13-8), (A1-44)+(S14-1), (A1-44)+(S14-2), (A1-44)+(S14-3), (A1-45)+(S1-1), (A1-45)+(S1-7), (A1-45)+(S1-11), (A1-45)+(S2-1), (A1-45)+(S3-1), (A1-45)+(S3-2), (A1-45)+(S3-4), (A1-45)+(S3-7), (A1-45)+(S3-8), (A1-45)+(S3-10), (A1-45)+(S3-11), (A1-45)+(S4-1), (A1-45)+(S4-5), (A1-45)+(S4-6), (A1-45)+(S11-1), (A1-45)+(S11-2), (A1-45)+(S11-3), (A1-45)+(S13-1), (A1-45)+(S13-2), (A1-45)+(S13-3), (A1-45)+(S13-8), (A1-45)+(S14-1), (A1-45)+(S14-2), (A1-45)+(S14-3), (A1-46)+(S1-1), (A1-46)+(S1-7), (A1-46)+(S1-11), (A1-46)+(S2-1), (A1-46)+(S3-1), (A1-46)+(S3-2), (A1-46)+(S3-4), (A1-46)+(S3-7), (A1-46)+(S3-8), (A1-46)+(S3-10), (A1-46)+(S3-11), (A1-46)+(S4-1), (A1-46)+(S4-5), (A1-46)+(S4-6), (A1-46)+(S11-1), (A1-46)+(S11-2), (A1-46)+(S11-3), (A1-46)+(S13-1), (A1-46)+(S13-2), (A1-46)+(S13-3), (A1-46)+(S13-8), (A1-46)+(S14-1), (A1-46)+(S14-2), (A1-46)+(S14-3), (A1-47)+(S1-1), (A1-47)+(S1-7), (A1-47)+(S1-11), (A1-47)+(S2-1), (A1-47)+(S3-1), (A1-47)+(S3-2), (A1-47)+(S3-4), (A1-47)+(S3-7), (A1-47)+(S3-8), (A1-47)+(S3-10), (A1-47)+(S3-11), (A1-47)+(S4-1), (A1-47)+(S4-5), (A1-47)+(S4-6), (A1-47)+(S11-1), (A1-47)+(S11-2), (A1-47)+(S11-

3), (A1-47)+(S13-1), (A1-47)+(S13-2), (A1-47)+(S13-3), (A1-47)+(S13-8), (A1-47)+(S14-1), (A1-47)+(S14-2), (A1-47)+(S14-3), (A1-48)+(S1-1), (A1-48)+(S1-7), (A1-48)+(S1-11), (A1-48)+(S2-1), (A1-48)+(S3-1), (A1-48)+(S3-2), (A1-48)+(S3-4), (A1-48)+(S3-7), (A1-48)+(S3-8), (A1-48)+(S3-10), (A1-48)+(S3-11), (A1-48)+(S4-1), (A1-48)+(S4-5), (A1-48)+(S4-6), (A1-48)+(S11-1), (A1-48)+(S11-2), (A1-48)+(S11-3), (A1-48)+(S13-1), (A1-48)+(S13-2), (A1-48)+(S13-3), (A1-48)+(S13-8), (A1-48)+(S14-1), (A1-48)+(S14-2), (A1-48)+(S14-3), (A1-49)+(S1-1), (A1-49)+(S1-7), (A1-49)+(S1-11), (A1-49)+(S2-1), (A1-49)+(S3-1), (A1-49)+(S3-2), (A1-49)+(S3-4), (A1-49)+(S3-7), (A1-49)+(S3-8), (A1-49)+(S3-10), (A1-49)+(S3-11), (A1-49)+(S4-1), (A1-49)+(S4-5), (A1-49)+(S4-6), (A1-49)+(S11-1), (A1-49)+(S11-2), (A1-49)+(S11-3), (A1-49)+(S13-1), (A1-49)+(S13-2), (A1-49)+(S13-3), (A1-49)+(S13-8), (A1-49)+(S14-1), (A1-49)+(S14-2), (A1-49)+(S14-3), (A1-50)+(S1-1), (A1-50)+(S1-7), (A1-50)+(S1-11), (A1-50)+(S2-1), (A1-50)+(S3-1), (A1-50)+(S3-2), (A1-50)+(S3-4), (A1-50)+(S3-7), (A1-50)+(S3-8), (A1-50)+(S3-10), (A1-50)+(S3-11), (A1-50)+(S4-1), (A1-50)+(S4-5), (A1-50)+(S4-6), (A1-50)+(S11-1), (A1-50)+(S11-2), (A1-50)+(S11-3), (A1-50)+(S13-1), (A1-50)+(S13-2), (A1-50)+(S13-3), (A1-50)+(S13-8), (A1-50)+(S14-1), (A1-50)+(S14-2), (A1-50)+(S14-3), (A1-51)+(S1-1), (A1-51)+(S1-7), (A1-51)+(S1-11), (A1-51)+(S2-1), (A1-51)+(S3-1), (A1-51)+(S3-2), (A1-51)+(S3-4), (A1-51)+(S3-7), (A1-51)+(S3-8), (A1-51)+(S3-10), (A1-51)+(S3-11), (A1-51)+(S4-1), (A1-51)+(S4-5), (A1-51)+(S4-6), (A1-51)+(S11-1), (A1-51)+(S11-2), (A1-51)+(S11-3), (A1-51)+(S13-1), (A1-51)+(S13-2), (A1-51)+(S13-3), (A1-51)+(S13-8), (A1-51)+(S14-1), (A1-51)+(S14-2), (A1-51)+(S14-3), (A1-52)+(S1-1), (A1-52)+(S1-7), (A1-52)+(S1-11), (A1-52)+(S2-1), (A1-52)+(S3-1), (A1-52)+(S3-2), (A1-52)+(S3-4), (A1-52)+(S3-7), (A1-52)+(S3-8), (A1-52)+(S3-10), (A1-52)+(S3-11), (A1-52)+(S4-1), (A1-52)+(S4-5), (A1-52)+(S4-6), (A1-52)+(S11-1), (A1-52)+(S11-2), (A1-52)+(S11-3), (A1-52)+(S13-1), (A1-52)+(S13-2), (A1-52)+(S13-3), (A1-52)+(S13-8), (A1-52)+(S14-1), (A1-52)+(S14-2), (A1-52)+(S14-3), (A1-53)+(S1-1), (A1-53)+(S1-7), (A1-53)+(S1-11), (A1-53)+(S2-1), (A1-53)+(S3-1), (A1-53)+(S3-2), (A1-53)+(S3-4), (A1-53)+(S3-7), (A1-53)+(S3-8), (A1-53)+(S3-10), (A1-53)+(S3-11), (A1-53)+(S4-1), (A1-53)+(S4-5), (A1-53)+(S4-6), (A1-53)+(S11-1), (A1-53)+(S11-2), (A1-53)+(S11-3), (A1-53)+(S13-1), (A1-53)+(S13-2), (A1-53)+(S13-3), (A1-53)+(S13-8), (A1-53)+(S14-1), (A1-53)+(S14-2), (A1-53)+(S14-3), (A1-54)+(S1-1), (A1-54)+(S1-7), (A1-54)+(S1-11), (A1-54)+(S2-1), (A1-54)+(S3-1), (A1-54)+(S3-2), (A1-54)+(S3-4), (A1-54)+(S3-7), (A1-54)+(S3-8), (A1-54)+(S3-10), (A1-54)+(S3-11), (A1-54)+(S4-1), (A1-54)+(S4-5), (A1-54)+(S4-6), (A1-54)+(S11-1), (A1-54)+(S11-2), (A1-54)+(S11-3), (A1-54)+(S13-1), (A1-54)+(S13-2), (A1-54)+(S13-3), (A1-54)+(S13-8), (A1-54)+(S14-1), (A1-54)+(S14-2), (A1-54)+(S14-3), (A1-55)+(S1-1), (A1-55)+(S1-7), (A1-55)+(S1-11), (A1-55)+(S2-1), (A1-55)+(S3-1), (A1-55)+(S3-2), (A1-55)+(S3-4), (A1-55)+(S3-7), (A1-55)+(S3-8), (A1-55)+(S3-10), (A1-55)+(S3-11), (A1-55)+(S4-1), (A1-55)+(S4-5), (A1-55)+(S4-6), (A1-55)+(S11-1), (A1-55)+(S11-2), (A1-55)+(S11-3), (A1-55)+(S13-1), (A1-55)+(S13-2), (A1-55)+(S13-3), (A1-55)+(S13-8), (A1-55)+(S14-1), (A1-55)+(S14-2), (A1-55)+(S14-3), (A1-56)+(S1-1), (A1-56)+(S1-7), (A1-56)+(S1-11), (A1-56)+(S2-1), (A1-56)+(S3-1), (A1-56)+(S3-2), (A1-56)+(S3-4), (A1-56)+(S3-7), (A1-56)+(S3-8), (A1-56)+(S3-10), (A1-56)+(S3-11), (A1-56)+(S4-1), (A1-56)+(S4-5), (A1-56)+(S4-6), (A1-56)+(S11-1), (A1-56)+(S11-2), (A1-56)+(S11-3), (A1-56)+(S13-1), (A1-56)+(S13-2), (A1-56)+(S13-3), (A1-56)+(S13-8), (A1-56)+(S14-1), (A1-56)+(S14-2), (A1-56)+(S14-3), (A1-57)+(S1-1), (A1-57)+(S1-7), (A1-57)+(S1-11), (A1-57)+(S2-1), (A1-57)+(S3-1), (A1-57)+(S3-2), (A1-57)+(S3-4), (A1-57)+(S3-7), (A1-57)+(S3-8), (A1-57)+(S3-10), (A1-57)+(S3-11), (A1-57)+(S4-1), (A1-57)+(S4-5), (A1-57)+(S4-6), (A1-57)+(S11-1), (A1-57)+(S11-2), (A1-57)+(S11-3), (A1-57)+(S13-1), (A1-57)+(S13-2), (A1-57)+(S13-3), (A1-57)+(S13-8), (A1-57)+(S14-1), (A1-57)+(S14-2), (A1-57)+(S14-3), (A1-58)+(S1-1), (A1-58)+(S1-7), (A1-58)+(S1-11), (A1-58)+(S2-1), (A1-58)+(S3-1), (A1-58)+(S3-2), (A1-58)+(S3-4), (A1-58)+(S3-7), (A1-58)+(S3-8), (A1-58)+(S3-10), (A1-58)+(S3-11), (A1-58)+(S4-1), (A1-58)+(S4-5), (A1-58)+(S4-6), (A1-58)+(S11-1), (A1-58)+(S11-2), (A1-58)+(S11-3), (A1-58)+(S13-1), (A1-58)+(S13-2), (A1-58)+(S13-3), (A1-58)+(S13-8), (A1-58)+(S14-1), (A1-58)+(S14-2), (A1-58)+(S14-3), (A1-59)+(S1-1), (A1-59)+(S1-7), (A1-59)+(S1-11), (A1-59)+(S2-1), (A1-59)+(S3-1), (A1-59)+(S3-2), (A1-59)+(S3-4), (A1-59)+(S3-7), (A1-59)+(S3-8), (A1-59)+(S3-10), (A1-59)+(S3-11), (A1-59)+(S4-1), (A1-59)+(S4-5), (A1-59)+(S4-6), (A1-59)+(S11-1), (A1-59)+(S11-2), (A1-59)+(S11-3), (A1-59)+(S13-1), (A1-59)+(S13-2), (A1-59)+(S13-3), (A1-59)+(S13-8), (A1-59)+(S14-1), (A1-59)+(S14-2), (A1-59)+(S14-3), (A1-60)+(S1-1), (A1-60)+(S1-7), (A1-60)+(S1-11), (A1-60)+(S2-1), (A1-60)+(S3-1), (A1-60)+(S3-2), (A1-60)+(S3-4), (A1-60)+(S3-7), (A1-60)+(S3-8), (A1-60)+(S3-10), (A1-60)+(S3-11), (A1-60)+(S4-1), (A1-60)+(S4-5), (A1-60)+(S4-6), (A1-60)+(S11-1), (A1-60)+(S11-2), (A1-60)+(S11-3), (A1-60)+(S13-1), (A1-60)+(S13-2), (A1-60)+(S13-3), (A1-60)+(S13-8), (A1-60)+(S14-1), (A1-60)+(S14-2), (A1-60)+(S14-3), (A1-61)+(S1-1), (A1-61)+(S1-7), (A1-61)+(S1-11), (A1-61)+(S2-1), (A1-61)+(S3-1), (A1-61)+(S3-2), (A1-61)+(S3-4), (A1-61)+(S3-7), (A1-61)+(S3-8), (A1-61)+(S3-10), (A1-61)+(S3-11), (A1-61)+(S4-1), (A1-61)+(S4-5), (A1-61)+(S4-6), (A1-61)+(S11-1), (A1-61)+(S11-2), (A1-61)+(S11-3), (A1-61)+(S13-1), (A1-61)+(S13-2), (A1-61)+(S13-3), (A1-61)+(S13-8), (A1-61)+(S14-1), (A1-61)+(S14-2), (A1-61)+(S14-3), (A1-62)+(S1-1), (A1-62)+(S1-7), (A1-62)+(S1-11), (A1-62)+(S2-1), (A1-62)+(S3-1), (A1-62)+(S3-2), (A1-62)+(S3-4), (A1-62)+(S3-7), (A1-62)+(S3-8), (A1-62)+(S3-10), (A1-62)+(S3-11), (A1-62)+(S4-1), (A1-62)+(S4-5), (A1-62)+(S4-6), (A1-62)+(S11-1), (A1-62)+(S11-2), (A1-62)+(S11-3), (A1-62)+(S13-1), (A1-62)+(S13-2), (A1-62)+(S13-3), (A1-62)+(S13-8), (A1-62)+(S14-1), (A1-62)+(S14-2), (A1-62)+(S14-3), (A1-63)+(S1-1), (A1-63)+(S1-7), (A1-63)+(S1-11), (A1-63)+(S2-1), (A1-63)+(S3-1), (A1-63)+(S3-2), (A1-63)+(S3-4), (A1-63)+(S3-7), (A1-63)+(S3-8), (A1-63)+(S3-10), (A1-63)+(S3-11), (A1-63)+(S4-1), (A1-63)+(S4-5), (A1-63)+(S4-6), (A1-63)+(S11-1), (A1-63)+(S11-2), (A1-63)+(S11-3), (A1-63)+(S13-1), (A1-63)+(S13-2), (A1-63)+(S13-3), (A1-63)+(S13-8), (A1-63)+(S14-1), (A1-63)+(S14-2), (A1-63)+(S14-3), (A2-1)+(S1-1), (A2-1)+(S1-7), (A2-1)+(S1-11), (A2-1)+(S2-1), (A2-1)+(S3-1), (A2-1)+(S3-2), (A2-1)+(S3-4), (A2-1)+(S3-7), (A2-1)+(S3-8), (A2-1)+(S3-10), (A2-1)+(S3-11), (A2-1)+(S4-1), (A2-1)+(S4-5), (A2-1)+(S4-6), (A2-1)+
(S11-1), (A2-1)+(S11-2), (A2-1)+(S11-3), (A2-1)+(S13-1),
(A2-1)+(S13-2), (A2-1)+(S13-3), (A2-1)+(S13-8), (A2-1)+
(S14-1), (A2-1)+(S14-2), (A2-1)+(S14-3),
(A2-2)+(S1-1), (A2-2)+(S1-7), (A2-2)+(S1-11), (A2-2)+
(S2-1), (A2-2)+(S3-1), (A2-2)+(S3-2), (A2-2)+(S3-4), (A2-
2)+(S3-7), (A2-2)+(S3-8), (A2-2)+(S3-10), (A2-2)+(S3-11),
(A2-2)+(S4-1), (A2-2)+(S4-5), (A2-2)+(S4-6), (A2-2)+
(S11-1), (A2-2)+(S11-2), (A2-2)+(S11-3), (A2-2)+(S13-1),
(A2-2)+(S13-2), (A2-2)+(S13-3), (A2-2)+(S13-8), (A2-2)+
(S14-1), (A2-2)+(S14-2), (A2-2)+(S14-3),
(A2-3)+(S1-1), (A2-3)+(S1-7), (A2-3)+(S1-11), (A2-3)+
(S2-1), (A2-3)+(S3-1), (A2-3)+(S3-2), (A2-3)+(S3-4), (A2-
3)+(S3-7), (A2-3)+(S3-8), (A2-3)+(S3-10), (A2-3)+(S3-11),
(A2-3)+(S4-1), (A2-3)+(S4-5), (A2-3)+(S4-6), (A2-3)+
(S11-1), (A2-3)+(S11-2), (A2-3)+(S11-3), (A2-3)+(S13-1),
(A2-3)+(S13-2), (A2-3)+(S13-3), (A2-3)+(S13-8), (A2-3)+
(S14-1), (A2-3)+(S14-2), (A2-3)+(S14-3),
(A2-4)+(S1-1), (A2-4)+(S1-7), (A2-4)+(S1-11), (A2-4)+
(S2-1), (A2-4)+(S3-1), (A2-4)+(S3-2), (A2-4)+(S3-4), (A2-
4)+(S3-7), (A2-4)+(S3-8), (A2-4)+(S3-10), (A2-4)+(S3-11),
(A2-4)+(S4-1), (A2-4)+(S4-5), (A2-4)+(S4-6), (A2-4)+
(S11-1), (A2-4)+(S11-2), (A2-4)+(S11-3), (A2-4)+(S13-1),
(A2-4)+(S13-2), (A2-4)+(S13-3), (A2-4)+(S13-8), (A2-4)+
(S14-1), (A2-4)+(S14-2) and (A2-4)+(S14-3).

In the context of the present invention, especially preferred compositions of the herbicides (A) are those with the following safeners: yr-diethyl, fenchlorazole, isoxadifen-ethyl, cloquintocet-mexyl, dichlormid, 3-dichloroacetyl-2,2,5-trimethyl-1,3-oxazolidine, benoxacor, 3-dichloroacetyl-1-oxa-3-azaspiro[4.5]decane, 1-dichloroacetylazepane, furilazole, ((R)-3-dichloroacetyl-5-(2-furyl)-2,2-dimethyl-oxazolidine), cyprosulfamide, N-isopropyl-4-sulfamoylbenzamide-1-(2-methoxyphenyl)ethanone, 1-[4-(N-2-methoxy-benzoylsulfamoyl)phenyl]-3-methylurea, oxabetrinil, fluxofenim, cyometrinil, 1,8-naphthalenedicarboxylic anhydride, fenclorim, flurazole, dietholate, dimepiperate, daimuron and cumyluron.

In the context of the present invention, very particular preference is given to compositions of the herbicides (A) with the following safeners: daimuron, benoxacor, furilazole, fluxofenim, fenchlorazole (ethyl ester), mefenpyr-diethyl, cloquintocet-mexyl, isoxadifen-ethyl, cyprosulfamide, flurazole, oxabetrinil, dichlormid and dietholate.

In the context of the present invention, even more preferred compositions of the herbicides (A) are those with the following safeners: mefenpyr-diethyl, isoxadifen-ethyl, cyprosulfamide, fenchlorazole ethyl ester, benoxacor, cloquintocet-mexyl, fluxofenim and furilazole.

Preference is given to herbicide-safener compositions comprising (A) a herbicidally active amount of one or more compounds of the formula (I) or salts thereof and (B) an antidotically active amount of one or more safeners.

Herbicidally active amount in the sense of the invention is an amount of one or more herbicides suitable for having an adverse impact on plant growth. An "antidotically active amount" in the context of the invention means an amount of one or more safeners suitable for reducing the phytotoxic effect of active ingredients of crop protection compositions (for example of herbicides) on crop plants.

The safeners (B) are suitable for reduction of phytotoxic effects which can occur when herbicides of the general formula (I) are used in crops of useful plants, without significantly impairing the efficacy of these active herbicidal ingredients against harmful plants. As a result of this, it is possible to extend the field of use of conventional crop protection compositions quite considerably, for example to crops in which use of the herbicides has been possible to date only to a limited degree, if at all.

According to the indication and active herbicidal ingredient used, the application rates of the safeners required may vary within wide limits and are generally in the range from 0.001 to 5 kg, preferably 0.005 to 2.5 kg and particularly 0.05 to 0.5 kg of active ingredient per hectare.

The herbicides (A) and the safeners (B) can be deployed together (for example as a ready-made formulation or by the tank-mix method) or successively in any sequence, for example by application by spraying, watering and sprinkling, or by granule scattering. The weight ratio of herbicide of the general formula (I) (A):safener (B) may vary within wide limits and is preferably in the range from 1:10 000 to 10 000:1, especially from 1:1000 to 1000:1 and very particularly from 1:20 to 20:1. The amounts of the general formula (I) (A) and safener (B) which are optimal in each case depend on the type of herbicide used and the safener used and on the nature and development stage of the plant stock to be treated, and can be determined in each individual case by simple, routine preliminary tests.

According to their properties, the safeners (B) present in the inventive herbicide-safener compositions can each be used for pretreatment of the seed of the crop plant (for example for dressing of the seed) or introduced into the seed furrows prior to sowing or employed together with the herbicide prior to or after emergence of the plants. Pre-emergence treatment includes both the treatment of the area under cultivation (including any water present in the area under cultivation, for example in the case of applications to rice) prior to sowing and the treatment of the areas under cultivation in which seeds have been sown but which are not yet covered by growing plants. Preference is given to application together with the herbicide. For this purpose, it is possible to use tank-mixes or ready-made formulations.

In a preferred embodiment, the seed (for example grains, seeds or vegetative propagation organs such as tubers or budded parts of shoots) or seedlings are pretreated with the safeners (B), optionally in combination with other active agrochemical ingredients. For pretreatment of the seed, the active ingredients can be applied to the seed, for example by dressing, or the active ingredients and the seed can be added to water or other solvents, and the active ingredients can be taken up, for example, by adsorption or diffusion in a dipping process or by swelling or pre-germination. For pretreatment of seedlings, the young plants can be contacted with the safeners, optionally in combination with other active agrochemical ingredients, for example by spraying, dipping or watering, and then transplanted and optionally aftertreated with the herbicides (A).

The seed or seedlings can be treated with the safeners (B) alone or together with other active agrochemical ingredients—such as fungicides, insecticides or plant fortifiers, fertilizers or swelling and germination accelerators. After the pretreatment application, the safeners may subsequently be applied once again before, after or together with one or more herbicides (A), possibly also in combination with other known herbicides. The pretreatment of the seed or seedlings can achieve improved long-term action of the safeners.

The present invention thus further provides a method for controlling unwanted plants in plant crops, which is characterized in that the herbicides (A) and the safeners (B) of the inventive herbicide-safener compositions are deployed, for example separately or together, on the plants (for example harmful plants such as mono- or dicotyledonous weeds or unwanted crop plants), the seed (for example grains, seeds or vegetative propagation organs such as tubers or budded parts of shoots) or the area on which the plants grow (for example the area under cultivation). It is possible here to apply one or more safeners (B), preferably one or more compounds, especially one compound, from groups (S1) to (S15) before, after or simultaneously with the herbicide(s) of the general formula (I) (A) to the plants, the seed or the area on which the plants grow (for example the area under cultivation). In a preferred embodiment, the safeners (B) are used for seed treatment.

Unwanted plants are understood to mean all plants which grow at sites where they are unwanted. These may, for example, be harmful plants (for example monocotyledonous or dicotyledonous weeds or unwanted crop plants), including, for example, those which are resistant to certain active herbicidal compounds, such as glyphosate, atrazine, glufosinate or imidazolinone herbicides.

Monocotyledonous weeds are classified, for example in the genera *Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus, Apera.* Dicotyledonous weeds are classified, for example, in the genera *Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus, Taraxacum, Euphorbia.*

Preferably, in the method of the invention, an effective amount of the herbicides (A) and the safeners (B) for control of harmful plants is applied in plant crops, for example in economically important farm crops, e.g. monocotyledonous farm crops such as cereals (e.g. wheat, barley, rye, oats), rice, corn, millet/sorghum, or dicotyledonous farm crops such as sugar beet, oilseed rape, cotton, sunflower and legumes, for example of the genera *Glycine* (e.g. *Glycine max.* such as non-transgenic *Glycine max.* (e.g. conventional varieties such as STS varieties) or transgenic *Glycine max.* (e.g. RR soya or LL soya) and crosses thereof), *Phaseolus, Pisum, Vicia* and *Arachis,* or vegetable crops from various botanic groups, such as potato, leek, cabbage, carrot, tomato, onion, and permanent crops and plantation crops such as pome fruit and stone fruit, berries, grapes, hevea, bananas, sugar cane, coffee, tea, citrus, nut plantations, lawns, palm crops and forestry crops.

The invention also provides for the use of the inventive herbicide-safener compositions for controlling unwanted vegetation, preferably in plant crops.

The inventive herbicide-safener compositions can be produced by known processes, for example as mixed formulations of the individual components, optionally with further active ingredients, additives and/or customary formulation auxiliaries, which are then applied in a customary manner diluted with water, or as what are called tank-mixes by co-dilution of the separately formulated or partially separately formulated individual components with water. Likewise possible is the application at different times (split application) of the separately formulated or partially separately formulated individual components. It is also possible to apply the individual components or the herbicide-safener compositions in several portions (sequential application), for example pre-emergence applications followed by post-emergence applications, or early post-emergence applications followed by post-emergence applications at an intermediate or late stage. Preference is given to the joint or immediately successive application of the active ingredients in the respective composition.

The inventive herbicide-safener compositions can also be used for control of harmful plants in crops of genetically modified plants which are known or are yet to be developed.

In general, transgenic plants are characterized by particular advantageous properties, for example by resistances to certain pesticides, in particular certain herbicides, resistances to plant diseases or pathogens of plant diseases, such as certain insects or microorganisms such as fungi, bacteria or viruses. Other particular properties relate, for example, to the harvested material with regard to quantity, quality, storability, composition and specific constituents. For instance, there are known transgenic plants with an elevated starch content or altered starch quality, or those with a different fatty acid composition in the harvested material. Other particular properties may be tolerance or resistance to abiotic stressors, for example heat, low temperatures, drought, salinity and ultraviolet radiation.

Preference is given to the use of the inventive herbicide-safener compositions in economically important transgenic crops of useful plants and ornamentals, for example of cereals such as wheat, barley, rye, oats, millet/sorghum, rice, cassava and corn, or else crops of sugar beet, cotton, soybean, oilseed rape, potato, tomato, peas and other vegetables. The herbicides (A) can preferably be used in crops of useful plants which are resistant, or have been made resistant by recombinant means, to the phytotoxic effects of the herbicides.

Conventional ways of producing novel plants which have modified properties in comparison to plants which have occurred to date consist, for example, in traditional breeding methods and the generation of mutants. Alternatively, novel plants with modified properties can be generated with the aid of recombinant methods (see, for example, EP-A-0221044, EP-A-0131624). For example, there have been descriptions in several cases of:

genetic modifications of crop plants for the purpose of modifying the starch synthesized in the plants (for example WO 92/11376, WO 92/14827, WO 91/19806), transgenic crop plants which are resistant to particular herbicides of the glufosinate type (cf., for example, EP-A-0242236, EP-A-242246) or glyphosate type (WO 92/00377) or of the sulfonylurea type (EP-A-0257993, U.S. Pat. No. 5,013,659), transgenic crop plants, for example cotton, with the ability to produce *Bacillus thuringiensis* toxins (Bt toxins), which make the plants resistant to particular pests (EP-A-0142924, EP-A-0193259).

transgenic crop plants with a modified fatty acid composition (WO 91/13972), genetically modified crop plants with novel constituents or secondary metabolites, for example novel phytoalexins, which bring about an increased disease resistance (EPA 309862, EPA0464461), genetically modified plants having reduced photorespiration, which have higher yields and higher stress tolerance (EPA 0305398), transgenic crop plants which produce pharmaceutically or diagnostically important proteins ("molecular pharming"), transgenic crop plants which feature higher yields or better quality, transgenic crop plants which feature a combination, for example, of the abovementioned novel properties ("gene stacking").

Numerous molecular biology techniques which can be used to produce novel transgenic plants with modified properties are known in principle; see, for example, I. Potrykus and G. Spangenberg (eds.) Gene Transfer to Plants, Springer Lab Manual (1995), Springer Verlag Berlin, Heidelberg, or Christou, "Trends in Plant Science" 1 (1996) 423-431).

For such recombinant manipulations, nucleic acid molecules which allow mutagenesis or sequence alteration by recombination of DNA sequences can be introduced into plasmids. With the aid of standard methods, it is possible, for example, to undertake base exchanges, remove parts of sequences or add natural or synthetic sequences. For the joining of the DNA fragments to one another, adaptors or linkers can be attached to the fragments; see, for example, Sambrook et al., 1989, Molecular Cloning, A Laboratory Manual, 2nd ed. Cold Spring Harbor Laboratory Press, Cold Spring Harbor, N.Y.; or Winnacker "Gene und Klone" [Genes and Clones], VCH Weinheim 2nd edition 1996.

For example, the generation of plant cells with a reduced activity of a gene product can be achieved by expressing at least one corresponding antisense RNA, a sense RNA for achieving a cosuppression effect, or by expressing at least one suitably constructed ribozyme which specifically cleaves transcripts of the abovementioned gene product.

To this end, it is firstly possible to use DNA molecules which encompass the entire coding sequence of a gene product inclusive of any flanking sequences which may be present, and also DNA molecules which only encompass portions of the coding sequence, in which case it is necessary for these portions to be long enough to have an antisense effect in the cells. It is also possible to use DNA sequences which have a high degree of homology to the coding sequences of a gene product, but are not completely identical to them.

When expressing nucleic acid molecules in plants, the protein synthesized may be localized in any desired compartment of the plant cell. However, to achieve localization in a particular compartment, it is possible, for example, to join the coding region to DNA sequences which ensure localization in a particular compartment. Such sequences are known to those skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106). The nucleic acid molecules can also be expressed in the organelles of the plant cells.

The transgenic plant cells can be regenerated by known techniques to give rise to entire plants. In principle, the transgenic plants may be plants of any desired plant species, i.e. not only monocotyledonous but also dicotyledonous plants.

Thus, transgenic plants can be obtained whose properties are altered by overexpression, suppression or inhibition of homologous (=natural) genes or gene sequences or expression of heterologous (=foreign) genes or gene sequences.

Preferably, the inventive herbicide-safener compositions can be used in transgenic crops which are resistant to growth regulators, for example dicamba, or to herbicides which inhibit essential plant enzymes, for example acetolactate synthases (ALS), EPSP synthases, glutamine synthases (GS) or hydroxyphenylpyruvate dioxygenases (HPPD), or to herbicides from the group of the sulfonylureas, the glyphosates, glufosinates or benzoylisoxazoles and analogous active ingredients.

On employment of the inventive herbicide-safener compositions in transgenic crops, not only do the effects toward harmful plants observed in other crops occur, but often also effects which are specific to application in the particular transgenic crop, for example an altered or specifically widened spectrum of weeds which can be controlled, altered application rates which can be used for the application, preferably good combinability with the herbicides to which the transgenic crop is resistant, and influencing of growth and yield of the transgenic crop plants.

The invention therefore also provides for the use of the inventive herbicide-safener compositions for control of harmful plants in transgenic crop plants.

Preference is given to the use of the inventive compositions in economically important transgenic crops of useful plants and ornamentals, for example of cereals (e.g. wheat, barley, rye, oats), millet/sorghum, rice, cassava and corn, or else crops of sugar beet, cotton, soybean, oilseed rape, potato, tomato, peas and other vegetable crops.

The invention therefore also provides for the use of the inventive herbicide-safener compositions for control of harmful plants in transgenic crop plants or crop plants having tolerance through selective breeding.

The herbicides (A) and the safeners (B) can be converted together or separately to customary formulations, for example for application by spraying, watering, sprinkling and seed dressing, such as solutions, emulsions, suspensions, powders, foams, pastes, granules, aerosols, active ingredient-impregnated natural and synthetic substances, microencapsulations in polymeric substances. The formulations may comprise the customary auxiliaries and additives.

These formulations are produced in a known manner, for example by mixing the active ingredients with extenders, i.e. liquid solvents, pressurized liquefied gases and/or solid carriers, optionally with use of surfactants, i.e. emulsifiers and/or dispersants and/or foam formers.

If the extender used is water, it is also possible to use, for example, organic solvents as auxiliary solvents. Useful liquid solvents essentially include: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and the ethers and esters thereof, ketones such as acetone, methyl ethyl ketone, methyl isobutyl ketone or cyclohexanone, strongly polar solvents such as dimethylformamide or dimethyl sulfoxide, and water.

Useful solid carriers include: for example ammonium salts and ground natural minerals, such as kaolins, clays, talc, chalk, quartz, attapulgite, montmorillonite or diatomaceous earth, and ground synthetic minerals, such as finely divided silica, alumina and silicates; useful solid carriers for granules include: for example crushed and fractionated natural rocks, such as calcite, marble, pumice, sepiolite, dolomite and synthetic granules of inorganic and organic flours, and granules of organic material, such as sawdust, coconut shells, corn cobs and tobacco stalks; useful emulsifiers and/or foam formers include: for example nonionic and anionic emulsifiers, such as polyoxyethylene fatty acid esters, polyoxyethylene fatty alcohol ethers, e.g. alkylaryl polyglycol ethers, alkylsulfonates, alkylsulfates, arylsulfonates and protein hydrolyzates; useful dispersants include: for example lignosulfite waste liquors and methylcellulose. In the formulations, it is possible to use tackifiers such as carboxymethylcellulose, natural and synthetic polymers in the form of powders, granules or latices, such as gum arabic, polyvinyl alcohol and polyvinyl acetate, or else natural phospholipids such as cephalins and lecithins and synthetic phospholipids. Further additives may be mineral and vegetable oils.

It is possible to use colorants such as inorganic pigments, for example iron oxide, titanium oxide and Prussian blue, and organic colorants such as alizarin colorants, azo colorants and metal phthalocyanine colorants, and trace nutrients such as salts of iron, manganese, boron, copper, cobalt, molybdenum and zinc.

The formulations contain generally between 0.1 and 95 percent by weight of active ingredient, preferably between 0.5 and 90% by weight.

The herbicides (A) and the safeners (B) can also be used as such or in formulations thereof in a mixture with other active agrochemical ingredients, such as known herbicides, for controlling unwanted vegetation, for example for controlling weeds or for controlling unwanted crop plants, possible examples being ready-made formulations or tank-mixes.

Also possible are mixtures with other known active ingredients such as fungicides, insecticides, acaricides, nematicides, bird antifeedants, plant nutrients and soil improvers, and likewise with additives and formulation auxiliaries customary in crop protection.

The herbicides (A) and the safeners (B) can be used as such, in the form of formulations thereof or in the use forms prepared therefrom by further dilution, such as ready-to-use solutions, suspensions, emulsions, powders, pastes and granules.

Application is typically accomplished, for example, by watering, sprinkling, spraying, broadcasting.

The active ingredients can be deployed on the plants, plant parts, seed or area under cultivation (farmland), preferably on the seed or the green plants and plant parts, and optionally additionally to the farmland. One means of application is the co-deployment of the active ingredients in the form of tank-mixes, by mixing the optimally formulated concentrated formulations of the individual active ingredients together in the tank with water and deploying the spray liquor obtained.

A co-formulation of the inventive compositions of herbicide (A) and safener (B) has the advantage of easier applicability, because the amounts of the components can already be set in the optimal ratio with respect to one another. Moreover, the auxiliaries in the formulation can be optimized to one another.

Combination partners usable for the inventive herbicide-safener compositions in mixed formulations or in a tank-mix are, for example, known, preferably herbicidal, active ingredients based on inhibition of, for example, acetolactate synthase, acetyl coenzyme A carboxylase, PS I, PS II, HPPD, phytoene desaturase, protoporphyrinogen oxidase, glutamine synthetase, cellulose biosynthesis, 5-enolpyruvylshikimate-3-phosphate synthetase. Such compounds and also other usable compounds, some with an unknown or different mechanism of action, are described, for example, in Weed Research 26, 441-445 (1986), or in the handbook "The Pesticide Manual", 12th edition 2000, or 13th edition 2003 or 14th edition 2006/2007, or in the corresponding "e-Pesticide Manual", Version 5.0 (2008-10), each published by the British Crop Protection Council, (also referred to hereinafter as "PM"), and literature cited therein. Lists of common names are also available in "The Compendium of Pesticide Common Names" on the Internet. Examples of herbicides known from the literature which can be combined with the inventive herbicide-safener compositions include the active ingredients which follow (N.B.: The compounds are designated either by the common name according to the International Organization for Standardization (ISO) or by the chemical name, in some cases together with a standard code number, and always encompass all use forms, such as acids, salts, esters and isomers, such as stereoisomers and optical isomers. In this case, one or else, in some cases, more than one application form is mentioned.):

2,4-D, acetochlor, acifluorfen, acifluorfen-sodium, aclonifen, alachlor, alloxydim, alloxydim-sodium, ametryn, amicarbazone, amidosulfuron, aminopyralid, amitrole, anilofos, asulam, atrazine, azafenidin, azimsulfuron, beflubutamid, benazolin, benazolin-ethyl, benfuresate, bensulfuron-methyl, bentazone, benzfendizone, benzobicyclon, benzofenap, bifenox, bilanafos, bispyribac-sodium, bromacil, bromobutide, bromofenoxim, bromoxynil, butachlor, butafenacil, butenachlor, butralin, butroxydim, butylate, cafenstrole, carbetamide, carfentrazone-ethyl, chlomethoxyfen, chloridazon, chlorimuron-ethyl, chlornitrofen, chlortoluron, chlorsulfuron, cinidon-ethyl, cinmethylin, cinosulfuron, clefoxydim, clethodim, clodinafop-propargyl, clomazone, clomeprop, clopyralid, cloransulam-methyl, cumyluron, cyanazine, cyclosulfamuron, cycloxydim, cyhalofop-butyl, desmedipham, dicamba, dichlobenil, dichlorprop, dichlorprop-P, diclofop-methyl, diclosulam, difenzoquat, diflufenican, diflufenzopyr, dikegulac-sodium, dimefuron, dimepiperate, dimethachlor, dimethametryn, dimethenamid, triaziflam, diquat-dibromide, dithiopyr, diuron, dymron, EPTC, esprocarb, ethalfluralin, ethametsulfuron-methyl, ethofumesate, ethoxyfen, ethoxysulfuron, etobenzanid, fenoxaprop-ethyl, fenoxaprop-P-ethyl, fentrazamide, flamprop-M-isopropyl, flamprop-M-methyl, flazasulfuron, florasulam, fluazifop, fluazifop-butyl, fluazifop-P-butyl, fluazolate, flucarbazone-sodium, flucetosulfuron, fluchloralin, flufenacet, flufenpyr, flumetsulam, flumiclorac-pentyl, flumioxazin, fluometuron, fluorchloridone, fluorglycofen-ethyl, flupoxam, flupyrsulfuron-methyl-sodium, fluridone, fluroxypyr, fluroxypyr-butoxypropyl, fluroxypyr-meptyl, flurprimidol, flurtamone, fluthiacet-methyl, fomesafen, foramsulfuron, glufosinate, glufosinate-P, glufosinate-ammonium, glufosinate-P-ammonium, glufosinate-P-sodium, glyphosate, halosulfuron-methyl, haloxyfop, haloxyfop-ethoxyethyl, haloxyfop-methyl, haloxyfop-P-methyl, hexazinone, imazamethabenz-methyl, imazamox, imazapic, imazapyr, imazaquin, imazethapyr, imazosulfuron, indanofan, indaziflam, iodosulfuron-methyl-sodium, ioxynil, isoproturon, isouron, isoxaben, isoxachlortole, isoxaflutole, ketospiradox, lactofen, lenacil, linuron, MCPA, mecoprop, mecoprop-P, mefenacet, mesosulfuron-methyl, mesotrione, metamifop, metamitron, metazachlor, methabenzthiazuron, methiozolin, methyldymron, metobromuron, metolachlor, metosulam, metoxuron, metribuzin, metsulfuron-methyl, molinate, monolinuron, naproanilide, napropamide, neburon, nicosulfuron, norflurazon, orbencarb, oryzalin, oxadiargyl, oxadiazon, oxasulfuron, oxaziclomefone, oxyfluorfen, paraquat, pelargonic acid, pendimethalin, pendralin, penoxsulam, pentoxazone, pethoxamid, phenmedipham, picloram, picolinafen, pinoxaden, piperophos, pretilachlor, primisulfuron-methyl, profluazol, profoxydim, prometryn, propachlor, propanil, propaquizafop, propisochlor, propoxycarbazone-sodium, propyrisulfuron, propyzamide, prosulfocarb, prosulfuron, pyraclonil, pyraflufen-ethyl, pyrazolate, pyrazosulfuron-ethyl, pyrazoxyfen, pyribenzoxim, pyributicarb, pyridafol, pyridate, pyriftalid, pyriminobac-methyl, pyrithiobac-sodium, quinclorac, quinmerac, quinoclamine, quizalofop-ethyl, quizalofop-P-ethyl, quizalofop-P-tefuryl, rimsulfuron, sethoxydim, simazine, simetryn, S-metolachlor, sulcotrione, sulfentrazone, sulfometuron-methyl, sulfosate, sulfosulfuron, tebuthiuron, tepraloxydim, terbuthylazine, terbutryn, thenylchlor, thiazopyr, thifensulfuron-methyl, thiobencarb, tiocarbazil, tralkoxydim, triallate, triasulfuron, tribenuron-methyl, triclopyr, tridiphane, trifloxysulfuron, trifluralin, triflusulfuron-methyl and tritosulfuron.

Further possible mixing partners are
pyroxasulfone, pyroxsulam, orthosulfamuron, pyrimisulfan, prohexadione-calcium, bencarbazone, SYN-523, IDH-100, SYP-249, monosulfuron, ipfencarbazone (HOK-201), pyribambenz-isopropyl, tefuryltrione, bencarbazone, tembotrione, pyrasulfotole and thiencarbazone-methyl.

For application, the formulations in commercial form are, if appropriate, diluted in a customary manner, for example in the case of wettable powders, emulsifiable concentrates, dispersions and water-dispersible granules with water. Dust-type formulations, granules for soil application or granules for scattering and sprayable solutions are not normally diluted further with other inert substances prior to application.

Biological Examples

Post-Emergence Herbicide Action and Safener Action

Seeds or rhizome pieces of mono- and dicotyledonous harmful plants and of crop plants are placed in sandy loam in peat pots, covered with soil and grown in a greenhouse under good growth conditions. Alternatively, harmful plants which occur in paddy rice cultivation are cultivated in pots containing water to a depth of 2 cm above the soil surface. Ten to twenty days after sowing, the test plants are treated at the one- to three-leaf stage. The inventive herbicide-safener compositions formulated as water-soluble powders or suspensions and, in parallel tests, the correspondingly formulated individual active ingredients are sprayed onto the green plant parts in various dosages with a water application rate of 300 l/ha (converted) and, after the test plants have been left to stand in the greenhouse under optimal growth conditions for 21 days, the effect of the preparations is assessed visually compared to untreated controls. In the case of rice or in the case of harmful plants which occur in rice cultivation, the active ingredients are also added directly to the irrigation water (application in analogy to what is called granule application) or sprayed onto plants and into the irrigation water. The experiments show that the use of the inventive herbicide-safener compositions significantly reduces the damage to crop plants compared to the use of the individual herbicides without safener. At the same time, the effect of the herbicide on economically important harmful plants is not significantly impaired, if at all, and so good pre-emergence herbicidal action against a broad spectrum of weed grasses and broad-leaved weeds can be achieved. In some cases, enhanced efficacy was even found, meaning that an inventive herbicide-safener composition surprisingly exhibits higher herbicidal efficacy than each herbicide alone. The tables which follow list, by way of example, results for numerous inventive herbicide-safener compositions. What are reported here are the respective combinations of herbicide and safener and dosage thereof, and the reduction in damage to the crop plant compared to the sole use of the herbicide.

TABLE A

| Herbicide | Dosage [g/ha] | Safener | Dosage [g/ha] | Reduction in damage in CORN |
|---|---|---|---|---|
| A1-7 | 25 | S1-1 | 100 | 100% |
| A1-7 | 25 | S1-11 | 100 | 100% |
| A1-7 | 25 | S4-1 | 100 | 50% |
| A1-7 | 25 | S2-1 | 100 | 100% |
| A1-7 | 25 | S3-4 | 100 | 100% |
| A1-7 | 25 | S4-6 | 100 | 100% |
| A1-7 | 25 | S3-10 | 100 | 100% |
| A1-7 | 25 | S11-2 | 100 | 100% |
| A1-7 | 25 | S1-7 | 100 | 50% |
| A1-13 | 10 | S1-1 | 100 | 40% |
| A1-13 | 10 | S1-11 | 100 | 100% |
| A1-13 | 10 | S4-1 | 100 | 100% |
| A1-13 | 10 | S2-1 | 100 | 100% |
| A1-13 | 10 | S4-6 | 100 | 100% |
| A1-16 | 30 | S1-1 | 100 | 100% |
| A1-16 | 30 | S1-11 | 100 | 100% |
| A1-16 | 30 | S4-1 | 100 | 100% |
| A1-16 | 30 | S2-1 | 100 | 75% |
| A1-16 | 30 | S3-4 | 100 | 100% |
| A1-16 | 30 | S4-6 | 100 | 100% |
| A1-16 | 30 | S3-10 | 100 | 100% |
| A1-16 | 30 | S11-2 | 100 | 50% |
| A1-16 | 30 | S1-7 | 100 | 100% |
| A1-19 | 33 | S1-1 | 100 | 100% |
| A1-19 | 33 | S1-11 | 100 | 100% |
| A1-19 | 33 | S4-1 | 100 | 100% |
| A1-19 | 33 | S2-1 | 100 | 100% |
| A1-19 | 33 | S3-4 | 100 | 100% |
| A1-19 | 33 | S4-6 | 100 | 100% |
| A1-19 | 33 | S3-10 | 100 | 100% |
| A1-19 | 33 | S11-2 | 100 | 100% |
| A1-36 | 18 | S1-1 | 100 | 33% |
| A1-36 | 18 | S1-11 | 100 | 33% |
| A1-36 | 18 | S4-1 | 100 | 67% |
| A1-36 | 18 | S2-1 | 100 | 100% |
| A1-36 | 18 | S3-4 | 100 | 67% |
| A1-36 | 18 | S4-6 | 100 | 67% |
| A1-36 | 18 | S3-10 | 100 | 67% |
| A1-36 | 18 | S11-2 | 100 | 100% |
| A1-36 | 18 | S1-7 | 100 | 67% |
| A1-62 | 15 | S1-1 | 100 | 100% |
| A1-62 | 15 | S1-11 | 100 | 83% |
| A1-62 | 15 | S4-1 | 100 | 67% |
| A1-62 | 15 | S2-1 | 100 | 67% |
| A1-62 | 15 | S3-4 | 100 | 100% |
| A1-62 | 15 | S4-6 | 100 | 100% |
| A1-62 | 15 | S3-10 | 100 | 100% |
| A1-62 | 15 | S11-2 | 100 | 100% |
| A1-62 | 15 | S1-7 | 100 | 67% |
| A1-67 | 25 | S4-1 | 100 | 100% |
| A1-68 | 12.5 | S4-1 | 100 | 50% |
| A2-1 | 90 | S1-1 | 100 | 100% |
| A2-1 | 90 | S1-11 | 100 | 100% |
| A2-1 | 90 | S2-1 | 100 | 100% |
| A2-1 | 90 | S3-4 | 100 | 100% |
| A2-1 | 90 | S4-6 | 100 | 100% |
| A2-1 | 90 | S1-7 | 100 | 100% |

TABLE B

| Herbicide | Dosage [g/ha] | Safener | Dosage [g/ha] | Reduction in damage in BARLEY |
|---|---|---|---|---|
| A1-39 | 33 | S1-1 | 100 | 100% |
| A1-39 | 33 | S1-11 | 100 | 100% |
| A1-39 | 33 | S4-1 | 100 | 50% |
| A1-39 | 33 | S2-1 | 100 | 50% |
| A1-39 | 33 | S3-4 | 100 | 100% |
| A1-39 | 33 | S4-6 | 100 | 50% |
| A1-39 | 33 | S3-10 | 100 | 50% |
| A1-39 | 33 | S11-2 | 100 | 50% |
| A1-39 | 33 | S1-7 | 100 | 50% |
| A1-45 | 25 | S1-1 | 100 | 67% |
| A1-45 | 25 | S1-11 | 100 | 33% |

TABLE B-continued

| Herbicide | Dosage [g/ha] | Safener | Dosage [g/ha] | Reduction in damage in BARLEY |
|---|---|---|---|---|
| A1-45 | 25 | S4-1 | 100 | 33% |
| A1-45 | 25 | S2-1 | 100 | 100% |
| A1-45 | 25 | S3-4 | 100 | 67% |
| A1-45 | 25 | S4-6 | 100 | 67% |
| A1-45 | 25 | S3-10 | 100 | 67% |
| A1-45 | 25 | S11-2 | 100 | 33% |
| A1-57 | 25 | S1-1 | 100 | 80% |
| A1-57 | 25 | S1-11 | 100 | 80% |
| A1-57 | 25 | S4-1 | 100 | 40% |
| A1-57 | 25 | S2-1 | 100 | 60% |
| A1-57 | 25 | S3-4 | 100 | 60% |
| A1-57 | 25 | S4-6 | 100 | 40% |
| A1-57 | 25 | S3-10 | 100 | 60% |
| A1-57 | 25 | S11-2 | 100 | 40% |
| A1-57 | 25 | S1-7 | 100 | 40% |
| A1-63 | 10 | S1-1 | 100 | 100% |
| A1-63 | 10 | S1-11 | 100 | 100% |
| A1-63 | 10 | S4-1 | 100 | 100% |
| A1-63 | 10 | S2-1 | 100 | 100% |
| A1-63 | 10 | S3-4 | 100 | 100% |
| A1-63 | 10 | S4-6 | 100 | 100% |
| A1-63 | 10 | S3-10 | 100 | 50% |
| A1-63 | 10 | S11-2 | 100 | 100% |
| A1-63 | 10 | S1-7 | 100 | 100% |
| A1-64 | 12.5 | S1-1 | 100 | 40% |

Pre-Emergence Herbicide Action and Safener Action

Seeds or rhizome pieces of mono- and dicotyledonous weed plants and crop plants were placed in sandy loam in peat pots and covered with soil. The inventive herbicide-safener compositions formulated as water-soluble powders or suspensions and, in parallel tests, the correspondingly formulated individual active ingredients were then applied to the surface of the covering soil in various dosages at a water application rate of 600 to 800 l/ha (converted). After the treatment, the pots were placed in a greenhouse and kept under good growth conditions for the weeds and the crop plants. The plants or emergence damage were scored visually after the emergence of the test plants, after a trial time of 21 days, in comparison to untreated controls. The experiments show that the use of the inventive herbicide-safener compositions significantly reduces the damage to crop plants compared to the use of the individual herbicides without safener. At the same time, the effect of the herbicide on economically important harmful plants is not significantly impaired, if at all, and so good pre-emergence herbicidal action against a broad spectrum of weed grasses and broad-leaved weeds can be achieved. In some cases, enhanced efficacy was even found, meaning that an inventive herbicide-safener composition surprisingly exhibits higher herbicidal efficacy than each herbicide alone. The table which follow lists, by way of example, results for numerous inventive herbicide-safener compositions. What are reported here are the respective combinations of herbicide and safener and dosage thereof, and the reduction in damage to the crop plant compared to the sole use of the herbicide.

TABLE C

| Herbicide | Dosage [g/ha] | Safener | Dosage [g/ha] | Reduction in damage in CORN |
|---|---|---|---|---|
| A1-7 | 25 | S1-1 | 100 | 100% |
| A1-7 | 25 | S1-11 | 100 | 100% |
| A1-7 | 25 | S4-1 | 100 | 50% |
| A1-7 | 25 | S2-1 | 100 | 100% |
| A1-7 | 25 | S3-4 | 100 | 100% |
| A1-7 | 25 | S4-6 | 100 | 100% |
| A1-7 | 25 | S3-10 | 100 | 100% |
| A1-7 | 25 | S11-2 | 100 | 100% |
| A1-7 | 25 | S1-7 | 100 | 50% |
| A1-13 | 90 | S1-11 | 100 | 100% |
| A1-13 | 90 | S2-1 | 100 | 100% |
| A1-13 | 90 | S4-6 | 100 | 100% |
| A1-13 | 50 | S4-1 | 100 | 100% |
| A1-13 | 10 | S1-7 | 100 | 100% |
| A1-16 | 30 | S1-1 | 100 | 100% |
| A1-16 | 30 | S1-11 | 100 | 100% |
| A1-16 | 30 | S4-1 | 100 | 100% |
| A1-16 | 30 | S2-1 | 100 | 100% |
| A1-16 | 30 | S3-4 | 100 | 100% |
| A1-16 | 30 | S4-6 | 100 | 100% |
| A1-16 | 30 | S3-10 | 100 | 100% |
| A1-16 | 30 | S11-2 | 100 | 100% |
| A1-16 | 30 | S1-7 | 100 | 100% |
| A1-36 | 18 | S1-1 | 100 | 33% |
| A1-36 | 18 | S1-11 | 100 | 33% |
| A1-36 | 18 | S4-1 | 100 | 67% |
| A1-36 | 18 | S2-1 | 100 | 100% |
| A1-36 | 18 | S3-4 | 100 | 67% |
| A1-36 | 18 | S4-6 | 100 | 75% |
| A1-36 | 18 | S3-10 | 100 | 67% |
| A1-36 | 18 | S11-2 | 100 | 100% |
| A1-36 | 18 | S1-7 | 100 | 67% |
| A1-39 | 33 | S1-1 | 100 | 100% |
| A1-39 | 33 | S4-1 | 100 | 100% |
| A1-39 | 33 | S2-1 | 100 | 100% |
| A1-39 | 33 | S3-4 | 100 | 100% |
| A1-39 | 33 | S4-6 | 100 | 100% |
| A1-39 | 33 | S3-10 | 100 | 100% |
| A1-39 | 33 | S11-2 | 100 | 100% |
| A1-39 | 33 | S1-7 | 100 | 100% |
| A1-45 | 25 | S1-1 | 100 | 100% |
| A1-45 | 25 | S1-11 | 100 | 100% |
| A1-45 | 25 | S4-1 | 100 | 100% |
| A1-45 | 25 | S2-1 | 100 | 100% |
| A1-45 | 25 | S3-4 | 100 | 100% |
| A1-45 | 25 | S4-6 | 100 | 100% |
| A1-45 | 25 | S3-10 | 100 | 100% |
| A1-45 | 25 | S11-2 | 100 | 100% |
| A1-45 | 25 | S1-7 | 100 | 100% |
| A1-62 | 15 | S1-1 | 100 | 100% |
| A1-62 | 15 | S1-11 | 100 | 100% |
| A1-62 | 15 | S4-1 | 100 | 100% |
| A1-62 | 15 | S2-1 | 100 | 100% |
| A1-62 | 15 | S3-4 | 100 | 100% |
| A1-62 | 15 | S4-6 | 100 | 100% |
| A1-62 | 15 | S3-10 | 100 | 100% |
| A1-62 | 15 | S11-2 | 100 | 100% |
| A1-62 | 15 | S1-7 | 100 | 100% |
| A1-63 | 90 | S1-1 | 100 | 100% |
| A1-63 | 90 | S2-1 | 100 | 100% |
| A1-63 | 90 | S3-4 | 100 | 100% |
| A1-63 | 90 | S4-6 | 100 | 100% |
| A1-63 | 90 | S3-10 | 100 | 50% |
| A1-63 | 90 | S11-2 | 100 | 100% |
| A1-63 | 90 | S1-7 | 100 | 100% |
| A1-65 | 50 | S4-1 | 100 | 50% |
| A1-66 | 50 | S4-1 | 100 | 50% |

Seed Treatment

Crop plant seed grains were mixed and shaken well in bottles with the safeners formulated as suspension or emulsion concentrates and water, such that the seed grains were coated homogeneously with the formulation of the particular safener. The seed grains or the plants after emergence were then treated with herbicides by the pre-emergence or post-emergence method. Numerous inventive herbicide-safener compositions, for example of herbicide nos. A1-1, A1-3, A1-4, A1-7, A1-10, A1-13, A1-14, A1-30, A1-46, A1-52, A1-55, A1-57, A1-60, A1-61 and A2-1 with each of the safeners S1-1, S1-11, S4-1 and S2-1, showed good efficacy here with respect to crop plants such as corn, rice, wheat or barley, with simultaneously good herbicida efficacy against a broad spectrum of harmful plants.

The invention claimed is:

1. A herbicide-safener composition comprising
(A) one or more compounds of formula (I) or a salt thereof,

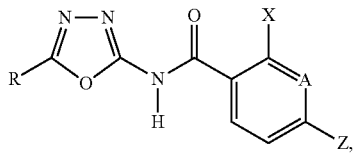

in which the symbols and indices are defined as follows:
A is N or CY,
R is methyl or $(CH_2)_2OMe$;
X is Cl or methyl;
Y is $OCH_2CF_3$, $OCH_2CH_2F$, $SO_2Me$, $SO_2Et$, O-nPr, or $SOCH_2c$-Pr
Z is $SO_2Me$ or $CF_3$;
and
(B) one or more safeners selected from S1-1: mefenpyr-diethyl, S1-7: fenchlorazol-ethyl, S1-11: isoxadifen-ethyl, S2-1: cloquintocet-mexyl, S3-4: benoxacor, S3-10: furilazole, S4-1: cyprosulfamide, S4-6:1-[4-(N-2-methoxybenzoylsulfamoyl)phenyl]-3-methylurea, or S11-2: oxabetrinil,
wherein the weight ratio of the compound of formula (I) (A) to safener (B) is in the range from 0.9:1 to 1:20.

2. The herbicide-safener composition as claimed in claim 1, in which
A is CY,
R is methyl
X is chlorine.

3. The herbicide-safener composition as claimed in claim 1, in which
A is N or CY,
R is Me.

4. The herbicide-safener composition as claimed in claim 1, comprising at least one safener which is mefenpyr-diethyl.

5. The herbicide-safener composition as claimed in claim 1, comprising at least one safener which is cyprosulfamide.

6. The herbicide-safener composition as claimed in claim 1, comprising at least one safener which is cloquintocet-mexyl.

7. A method for controlling harmful plants in crops of useful plants, comprising applying a herbicidally active amount of a composition as claimed in claim 1 to one or more harmful plants, plants, plant seeds and/or an area on which plants grow.

8. The method as claimed in claim 7, wherein the useful plants are selected from the group consisting of sugar cane, corn, wheat, rye, barley, oats, rice, sorghum, cotton and soya.

9. The method as claimed in claim 7 wherein the useful plants have been genetically modified.

10. The herbicide-safener composition as claimed in claim 1, in which
A is CY,
R is Me,
X is Me,
Y is $SO_2Me$, and
Z is $CF_3$.

11. The herbicide-safener composition as claimed in claim 1, wherein the safener is isoxadifen-ethyl.

12. The herbicide-safener composition as claimed in claim 1, in which
A is CY,
R is Me,
X is Me,
Y is $SO_2Me$,
Z is $CF_3$,
and the safener is isoxadifen-ethyl.

13. The herbicide-safener composition as claimed in claim 1 wherein the weight ratio of the compound of formula (I) (A) to safener (B) is in the range from 1:10 to 0.9:1.

14. The herbicide-safener composition as claimed in claim 6 wherein the weight ratio of the compound of formula (I) (A) to safener (B) is in the range from 1:10 to 0.9:1.

15. The herbicide-safener composition as claimed in claim 12 wherein the weight ratio of the compound of formula (I) (A) to safener (B) is in the range from 1:10 to 0.9:1.

* * * * *